(12) United States Patent
Cummings et al.

(10) Patent No.: US 7,189,828 B2
(45) Date of Patent: **\*Mar. 13, 2007**

(54) GLYCOSULFOPEPTIDE INHIBITORS OF LEUKOCYTE ROLLING AND METHODS OF USE THEREOF

(75) Inventors: Richard D. Cummings, Edmond, OK (US); Rodger P. McEver, Oklahoma City, OK (US)

(73) Assignee: The Board of Regents of The University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/239,576

(22) Filed: Sep. 29, 2005

(65) Prior Publication Data

US 2006/0024779 A1    Feb. 2, 2006

Related U.S. Application Data

(63) Continuation of application No. 10/278,594, filed on Oct. 18, 2002, now abandoned, which is a continuation-in-part of application No. 09/334,013, filed on Jun. 15, 1999, now Pat. No. 6,593,459, application No. 10/278,594, filed on Oct. 18, 2002.

(60) Provisional application No. 60/345,988, filed on Oct. 19, 2001, provisional application No. 60/089,472, filed on Jun. 16, 1998.

(51) Int. Cl.
*C07H 3/06* (2006.01)
*A61K 31/70* (2006.01)
*A61K 38/14* (2006.01)

(52) U.S. Cl. .................... 530/395; 530/324; 530/325; 530/326; 530/327; 530/322; 530/333; 530/344; 530/402; 530/412; 514/42; 514/8; 514/23; 514/25; 424/9.1

(58) Field of Classification Search ............... 530/395, 530/324, 325, 326, 327, 322, 333, 344, 402, 530/412; 514/42, 8, 23, 25; 424/9.1
See application file for complete search history.

(56) References Cited

U.S. PATENT DOCUMENTS

| | | | |
|---|---|---|---|
| 4,179,337 A | 12/1979 | Davis et al. |
| 5,047,335 A | 9/1991 | Paulson et al. |
| 5,180,674 A | 1/1993 | Roth |
| 5,382,657 A | 1/1995 | Karisiewicz et al. |
| 5,766,897 A | 6/1998 | Braxton |
| 5,821,329 A | 10/1998 | Lobl et al. |
| 5,827,817 A | 10/1998 | Larsen et al. |
| 5,858,994 A | 1/1999 | Kretzschmar et al. |
| 5,874,261 A | 2/1999 | Roth |
| 5,929,036 A | 7/1999 | McEver |
| 5,972,885 A | 10/1999 | Spira et al. |
| 6,136,790 A | 10/2000 | Toepfer et al. |
| 6,165,509 A | 12/2000 | Hoffman et al. |
| 6,177,087 B1 | 1/2001 | Greenwald et al. |
| 6,250,469 B1 | 6/2001 | Kline |
| 6,593,459 B1 | 7/2003 | Cummings et al. |
| 2002/0026033 A1 | 2/2002 | Cummings et al. |
| 2003/0130174 A1 | 7/2003 | Cummings et al. |
| 2003/0144183 A1 | 7/2003 | Cummings et al. |

FOREIGN PATENT DOCUMENTS

| | | |
|---|---|---|
| EP | 0577580 | 1/1994 |
| WO | 9411498 | 5/1994 |
| WO | 9706176 | 2/1997 |
| WO | PCT/US99/13455 | 6/1999 |
| WO | WO99/65712 | 12/1999 |
| WO | PCT/US02/33535 | 11/2003 |

OTHER PUBLICATIONS

Amado et Ali., "A Family of Human 3-galactosyltransferases," J. Biol. Chem., (May 22, 1998) 273 (21): 12770-12778.
Bierhuizen et al., "Expression Cloning of a cDNA encoding UDP-GlcNAc:Galβ1-3-GalNAc-R (GlcNAc to GalNAc) β1-6GlcNAc transferase by Gene Transfer Into CHO Cells Expressing Polyoma Large Tumor Antigen," Proc. Natl. Acad. Sci. USA, 89:9326-9330, Oct. 1992.
Brockhausen et al., "Control of 0-glycan synthesis: specificty and inhibition of 0-glycan core 1 UDP-galactose: N-acetylgalactosamine- -R3-galactosyltransferase from rat liver," Biochem, Cell Biol., (1992) 70: 99-108.
Brockhausen et al., "Enzymatic basis for sialyl-Tn expression in human colon cancer cells," Glycoconjugate Journal, (1998) 15:595-603.
Cheng et al., "Mucin Biosynthesis," J. Biol. Chem., (1982) 257 (11): 6251-6258.
Delhom et al., "Synthesis of Sulfated Bioactive Peptides Using Immobilized Arylsufotransferase from Eubacterium," sp. *Biotechnol. Lett.* May 1996, vol. 18, No. 5, pp. 609-614, entire document.
Granovsky et al., "UDPgalactose: glycoprotein-N-acetyl-D-galactosamine 3-3-D-galactosyltransferase activity synthesizing O-glycan core 1 is controlled by the amino acid sequence and glycosylation of glycopeptide substrates," Euro. J. Biochem., (1994) 22:1039-1046.
Harris et al., "Pegylation A Novel Process for Modifying Pharmacokinetics," Clin Pharmacokinet 2001; 40(7); 539-551.

(Continued)

*Primary Examiner*—Chih-Min Kam
(74) *Attorney, Agent, or Firm*—Dunlap, Codding & Rogers, P.C.

(57) ABSTRACT

Compounds, compositions and methods for treating conditions characterized by leukocyte rolling are described. The compounds contain glycosulfopeptide structures comprising sulfated tyrosines and sialylated, fucosylated N-acetyllactosamino glycans. The glycosulfopeptides may be conjugated or complexed to other compounds for enhancing serum half-life or for controlled release, for example. Examples of conditions treated include inflammation, ischemia-reperfusion injury, rheumatoid arthritis, atherosclerosis, leukocyte-mediated lung injury, restenosis, and thrombosis.

6 Claims, 17 Drawing Sheets

OTHER PUBLICATIONS

Hicks, et al., "Glycosulfopeptides modeled on P-selectin glycoprotein ligand 1 inhibit P-selectin-dependent leukocyte rolling in vivo", FASEB Journal, Sep. 2002, vol. 16, No. 11, pp. 1461-1462, especially p. 1462.

Hicks, et al., Glycosulfopeptides Modeled on PSGL-1 Inhibit P-selectin-dependent Leucocyte Rolling in Vivo. FASEB Journal, Mar. 2002, vol. 15, No. 5, p. A1052, see abstract.

Leppanen et al., "Binding of Glycosulopeptides to P-selectin Requires Stereospecific Contributions of Individual Tyrosine Sulfate and Sugar Residues" J. Biol. Chem., (2000) 275 (50): 39569-39578.

Leppanen et al., "A Novel Glycosulfopeptide Binds to P-selectin and Inhibits Leukocyte Adhesion to P-selectin" J. Biol. Chem., (1999) 274 (35): 24838-24848.

Lo-Guidice et al., "Sialylationa nd Sulfation of the Carbohydrate Chains in Respiratory Mucins from a Patient with Cystic Fibrosis," J. Biol. Chem., (Jul. 1994) 269 (29): 18794-18813.

Lopez et al., "O-Glycosylation potential of lepidopteran insect cell lines," Biochimica et Biophysica Acta (1999) 1427:49-61.

Meier et al., "The ELAM LIgand Fucosyltransferase, ELFT, Directs E-Selectin Binding to a Secreted Scaffold Protein: A Method to Produce and Purify Large Quantities of Specific Carbohydrate Structures," Chemical Abstracts, XP-002124245, 119(17), 20/25/93.

Moore et al., "The P-Selectin Glycoprotein Ligand From Human Neutrophils Displays Slalylated, Fucosylated, O-Linked Poly-N-Acetyllactosamine," The Journal of Biological Chemistry, 269(37):23318-23327, 1994.

Nishimune et al., "Detection of protein-protein interactionns in the nervous system using the two-hybrid system," Trends Neurosci. (1996) 19, 261-266.

Pouyani et al., "PSGL-1 Recvognition of P-Selectin is Controlled by a Tyrosine Sulfation Consensus at the PSGL-1 Amino Terminus," Cell. Oct. 20, 1995, vol. 83, No. 2, pp. 333-343, entire document.

Sako et al., "A sulfated Peptide Segment at the Amino Terminus of PSGL-1 is Critical for P-Selectin Binding," Cell. Oct. 20, 1995, vol. 83, No. 2, pp. 323-331, entire document.

Seitz et al., "Chemoenzymatic Solution- and Solid-Phase Synthesos of O-Glycopeptides of the Mucin Domain of MAdCAM-1, A General Route to O-LacNAc, O-Sialyl-LacNAc and O-Sialyl-Lewis-X Peptides," J. Am. Chem. Soc., 119:8766-8776, 1997.

Sueyoshi et al., "Expression of Distinct Fucosylated Ollgosaccharides and Carbohydrate-Mediated Adhesion Efficiency Directed by Two Different α-1,3-fucosyltransferases," The Journal of Biological Chemistry, 269(51):32342-32350, 1994.

Thurnher et al., "T cell clones with normal or defective O-galactosylation from a patient with permanent mixed-field polyagglutinability," Eur. J. Immunol., (1992) 22: 1835-1842.

Wilkins et al., Structures of the O-Glycans on P-Seletin Glycoprotein Ligand-1 from HL-60 Cells. Journal Biol. Chem. Aug. 2, 1996, vol. 271, No. 31, pp. 18732-18742, entire document.

Wilkins et al., "Tyrosine Sulfation of P-selectin Glycoprotein Ligand-1 Is Required for High Affinity Bnding to P-selectin," J. BIol. Chem., (1995), vol. 270, No. 39, pp. 22677-22680.

Wünsch et al., "Synthesis of Cholecystokinin-Related Peptides and Their Biological Properties," Biol. Chem. Hoppe-Seylor. Apr. 1989, vol. 370, pp. 317-321, entire document.

Yamamoto et al., "Chemoenzymatic Synthesis of a Novel Glycopeptide Using a Microbial Endoglycosidase," Caro. Res. Jan. 9, 1998, vol. 305, No. 3-4, pp. 415-422, entire document.

Graph showing the effects of 4-GSP-6 (1.43 µmol/kg) on P-selectin dependent rolling (rolling velocity)

Graph showing the effects of 4-GSP-6 (4.3 µmol/kg) on P-selectin dependent rolling (rolling velocity)

Graph showing the effects of 4-GSP-6 (12.9 μmol/kg) on P-selectin dependent rolling (rolling velocity)

PEG – GSP          A $PEG_2$ – GSP         B

PEG – GSP          C
      |
   $PEG_2$

PEG – GSP          D
      |
   PEG $PEG_2$ – GSP         E
       |
    $PEG_2$

FIG. 15

GLYCOSULFOPEPTIDE INHIBITORS OF LEUKOCYTE ROLLING AND METHODS OF USE THEREOF

CROSS-REFERENCE TO RELATED APPLICATIONS

The present application is a continuation of U.S. Ser. No. 10/278,594, filed Oct. 18, 2002, now abandoned, which is a continuation-in-part of U.S. Ser. No. 09/334,013, filed Jun. 15, 1999, now U.S. Pat. No. 6,593,459, which claims the benefit of U.S. Provisional Application Ser. No. 60/089,472, filed Jun. 16, 1998. U.S. Ser. No. 10/278,594 also claims the benefit of U.S. Provisional Application 60/345,988 filed Oct. 19, 2001. Each of the above applications are hereby incorporated by reference herein in their entirety.

STATEMENT REGARDING FEDERALLY SPONSORED RESEARCH OR DEVELOPMENT

This work was supported in part by NIH grants POIHL 54804, HL54502, and AI44902. The U.S. Government has certain rights to this invention.

BACKGROUND

The present invention is directed to glycosulfopeptides and methods of their use in treating inflammation and disorders related to leukocyte rolling mediated by P-selectin binding.

Inflammation is the reaction of vascularized tissue to local injury. This injury can have a variety of causes, including infections and direct physical injury. The inflammatory response can be considered beneficial, since without it, infections would go unchecked, wounds would never heal, and tissues and organs could be permanently damaged and death may ensue. However, the inflammatory response is also potentially harmful. Inflammation can generate pathology associated with rheumatoid arthritis, myocardial infarction, ischemia reperfusion injury, hypersensitivity reaction, and some types of fatal renal disease. The widespread problem of inflammatory diseases has fostered the development of many "anti-inflammatory" drugs. The ideal anti-inflammatory drug would be one that enhances the good effects resulting from the inflammatory response, and at the same time prevents or reduces the potentially harmful side-effects of this response.

The inflammatory response in regard to blood cells is accompanied by adhesion of circulating neutrophils, the most abundant phagocytic cell in the blood, to activated endothelial cells that line the vessels and make up the vessel walls. The adherent neutrophils are subsequently activated and the activated neutrophils emigrate from the blood into the surrounding tissue in a process termed diapedesis. The cells then begin engulfing microorganisms in a process termed phagocytosis and they also degranulate, releasing a variety of degradative enzymes, including proteolytic and oxidative enzymes into the surrounding extracellular environment. The mechanisms by which neutrophils adhere, become activated, and emigrate from the blood are currently major topics of research around the world.

Leukocyte recruitment to inflamed tissues is a highly ordered process that begins with and is to a large extent reliant on selectin-dependent leukocyte rolling. Inhibiting selectin binding therefore holds great promise for the treatment of inflammatory diseases and conditions. The selectin family of adhesion molecules has three functionally and structurally related members, namely E-selectin (expressed by endothelial cells) L-selectin (expressed by leukocytes) and P-selectin (expressed by endothelial cells and platelets). P-selectin has been convincingly implicated in inflammatory disorders including ischemia-reperfusion injury and atherosclerosis. Leukocyte rolling is supported by rapid formation of selectin-selectin ligand bonds at the front of a cell, coupled with detachment at the rear. With a constant requirement for new bond formation, leukocyte rolling is therefore sensitive to treatments that block the molecules involved in this response. In keeping with this model, application of antibodies that block the selectins or PSGL-1 (P-selectin glycoprotein ligand-1) should cause reversal of existing leukocyte rolling in vivo. Charged polysaccharides such as fucoidin and dextran sulfate can also inhibit preexisting leukocyte rolling, presumably by binding to and blocking the selecting.

The realization that the selectin family of adhesion molecules all recognize sialylated fucosylated glycans, prototypically represented by the tetrasaccharide sialyl Lewis$^x$ (sLe$^x$), fueled development of carbohydrate based selectin inhibitors. Data from in vitro binding assays and from models of inflammation support the notion that sLe$^x$-mimetic drugs inhibit all three selectins and, as such, should be efficacious against inflammatory disease. Using an intravital microscopy model, where leukocyte rolling was observed immediately before and after application of inhibitors, it was shown that sLe$^x$ and close structural mimetics thereof are, in fact, weak inhibitors of E-selectin dependent rolling and have no impact whatsoever on P- or L-selectin dependent rolling. This fact is consistent with the notion that sLe$^x$ and related structures represent only one component of the macromolecular assemblies that represent true selectin ligands.

The best characterized selectin ligand is PSGL-1, a dimeric mucin present on all leukocytes. Studies with antibodies and with gene-targeted mice lacking PSGL-1 have demonstrated that PSGL-1 is the major ligand for P-selectin dependent leukocyte rolling in the microcirculation. In addition, it was demonstrated that recombinant PSGL-1 fused to human IgG (rPSGL-Ig) could support rolling interactions of microspheres with E- and P-selectins in venules and could competitively inhibit leukocyte rolling on E- and L- as well as P-selectin in vivo. However, difficulties of large scale synthesis and fears of immune reactions limit the use of antibodies for therapy, whereas a high possibility of non-specific side effects limit the use of fucoidin and similar agents. Therefore, smaller molecules of defined structure that selectively bind to selectins with high affinity and which prevent binding of selectins to ligands could comprise attractive drug candidates.

BRIEF DESCRIPTION OF THE DRAWINGS

In FIGS. 4A and 4B glycosulfopeptide A is represented by SEQ ID NO:1, B by SEQ ID NO:2, C by SEQ ID NO:3, D by SEQ ID NO:4, E by SEQ ID NO:5, F by SEQ ID NO:6, G by SEQ ID NO:7, H by SEQ ID NO:8, I by SEQ ID NO:9, J by SEQ ID NO:10, K by SEQ ID NO:11, L by SEQ ID NO:12, M by SEQ ID NO:13 and N by SEQ ID NO:14.

FIG. 15 shows schematic structures of A–E of GSPs conjugated in several ways to PEG.

DETAILED DESCRIPTION OF THE INVENTION

Figure 1A:
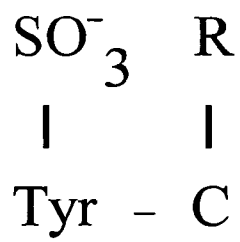
FIGS. 1A and 1B show formulas of glycosulfopeptides contemplated by the present invention wherein the R groups represented are those in FIGS. 5A–5C.

The present invention contemplates the use of a new class of synthetic glycosulfopeptides (GSPs) which comprise one or more sulfated tyrosine residues and a glycan comprising a sialyl Lewis$^x$ group or a sialyl Lewis$^a$ group. In a preferred embodiment, the GSPs further comprise an O-glycan comprising a β1,6 linkage to a GalNAc. The present invention contemplates methods of using these GSPs in vivo as powerful anti-inflammatory, antithrombotic, or anti-metastatic compounds which are able to block the selectin-mediated rolling and adhesion of leukocytes.

The present invention contemplates use of glycosulfopeptides which comprise at least one natural or synthetic amino acid residue able to provide a glycosidic linkage (e.g., including, but not limited to, serine, threonine, hydroxyproline, tyrosine, hydroxylysine, methionine, lysine, cysteine, asparagine, and glutamine). The peptide backbone of the GSP preferably comprises from two amino acids to 30 amino acids, and more particularly may comprise from 3 to 29 amino acid residues, 4 to 28 amino acid residues, 5 to 27 amino acid residues, 6 to 26 amino acid residues, 7 to 25 amino acid residues, 8 to 24 amino acid residues, 9 to 23 amino acid residues, 10 to 22 amino acid residues, 11 to 21 amino acid residues, 12 to 20 amino acid residues, 13 to 19 amino acid residues, 14 to 18 amino acid residues, 15 to 17 amino acid residues, or 16 amino acid residues.

The glycosulfopeptide contemplated herein preferably comprises at least one sulfated tyrosine residue, more preferably two sulfated tyrosine residues, and most preferably three sulfated tyrosine residues. The glycosulfopeptide contemplated herein may comprise four or five sulfated tyrosines. Each tyrosine residue is preferably separated by at least one additional amino acid residue. The glycosulfopeptide can be constructed by one of the methods described in the specifications of U.S. Ser. No. 09/849,031, U.S. Ser. No. 09/849,562, U.S. Ser. No. 09/334,013 filed Jun. 15, 1990 and U.S. Provisional Application 60/089,472 filed Jun. 16, 1998, each of which is hereby expressly incorporated by reference herein in its entirety.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

As noted, above, the glycosulfopeptides contemplated herein comprise at least one oligosaccharide conjugated to a linking amino acid on a peptide backbone thereof.

Figure 5A:
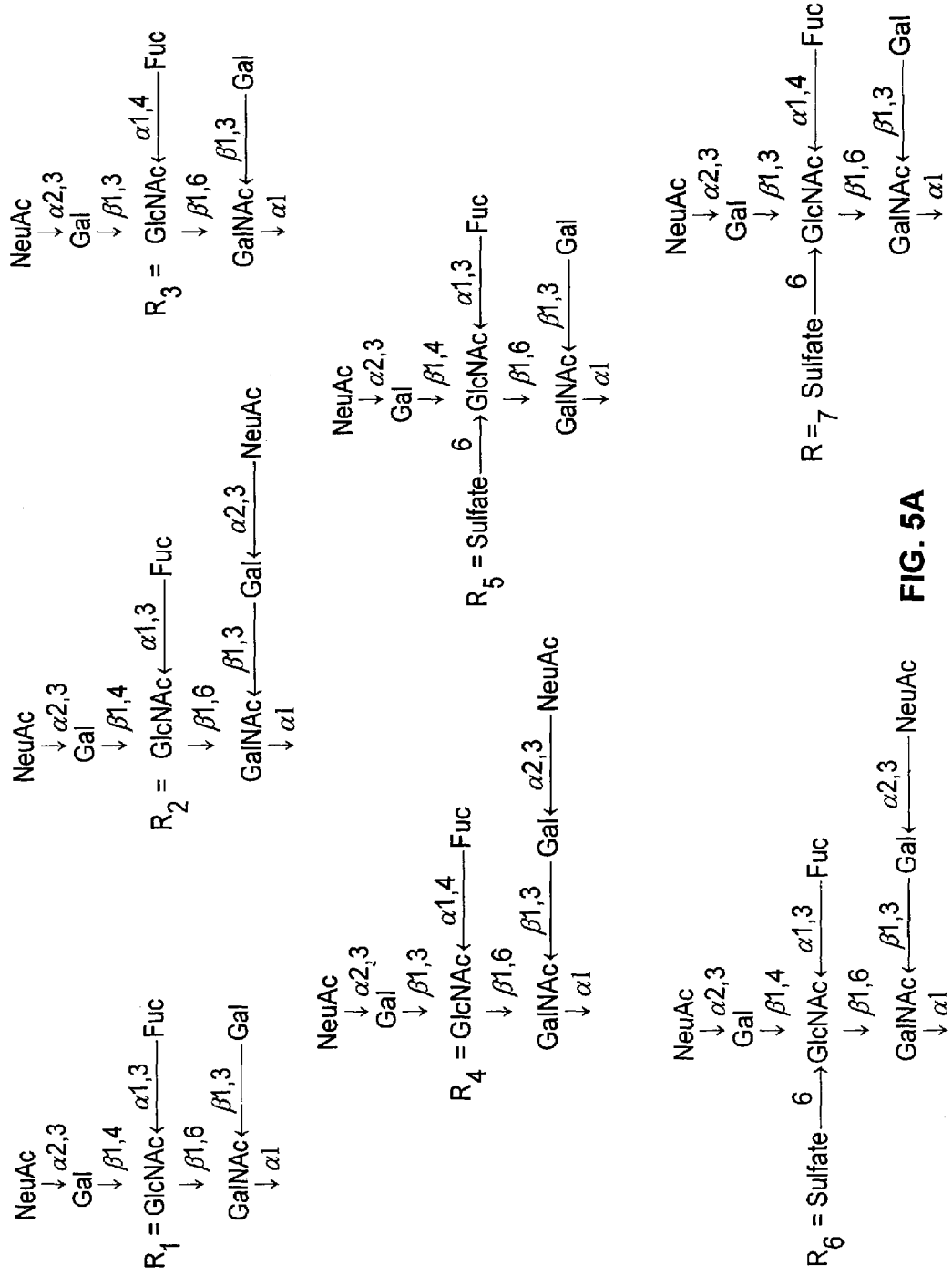
FIGS. 5A, 5B and 5C show chemical structures of a number of R groups which are among those which may comprise the glycan portion of the glycosulfopeptides contemplated by the present invention.
Figure 5B:
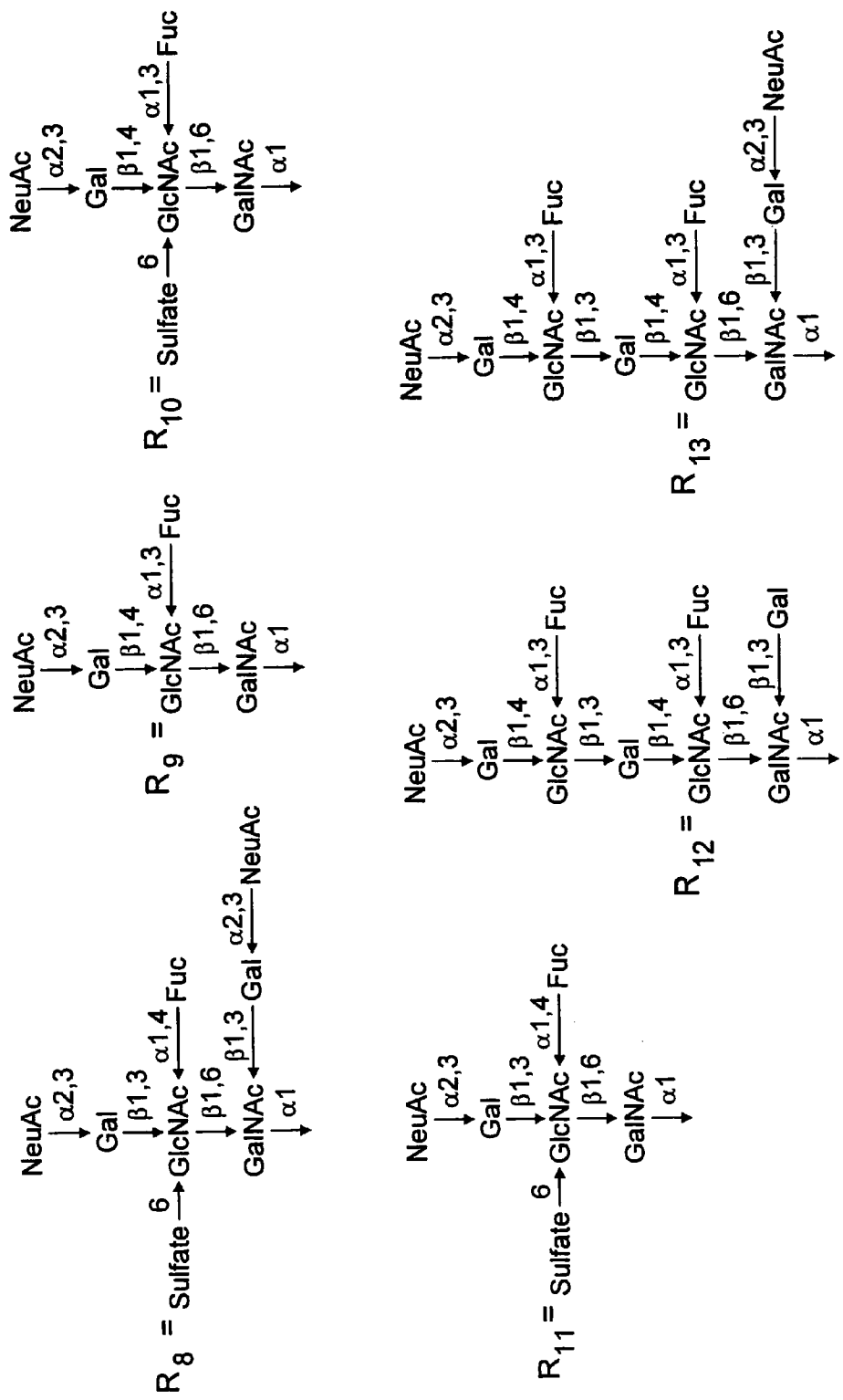
Figure 5C:
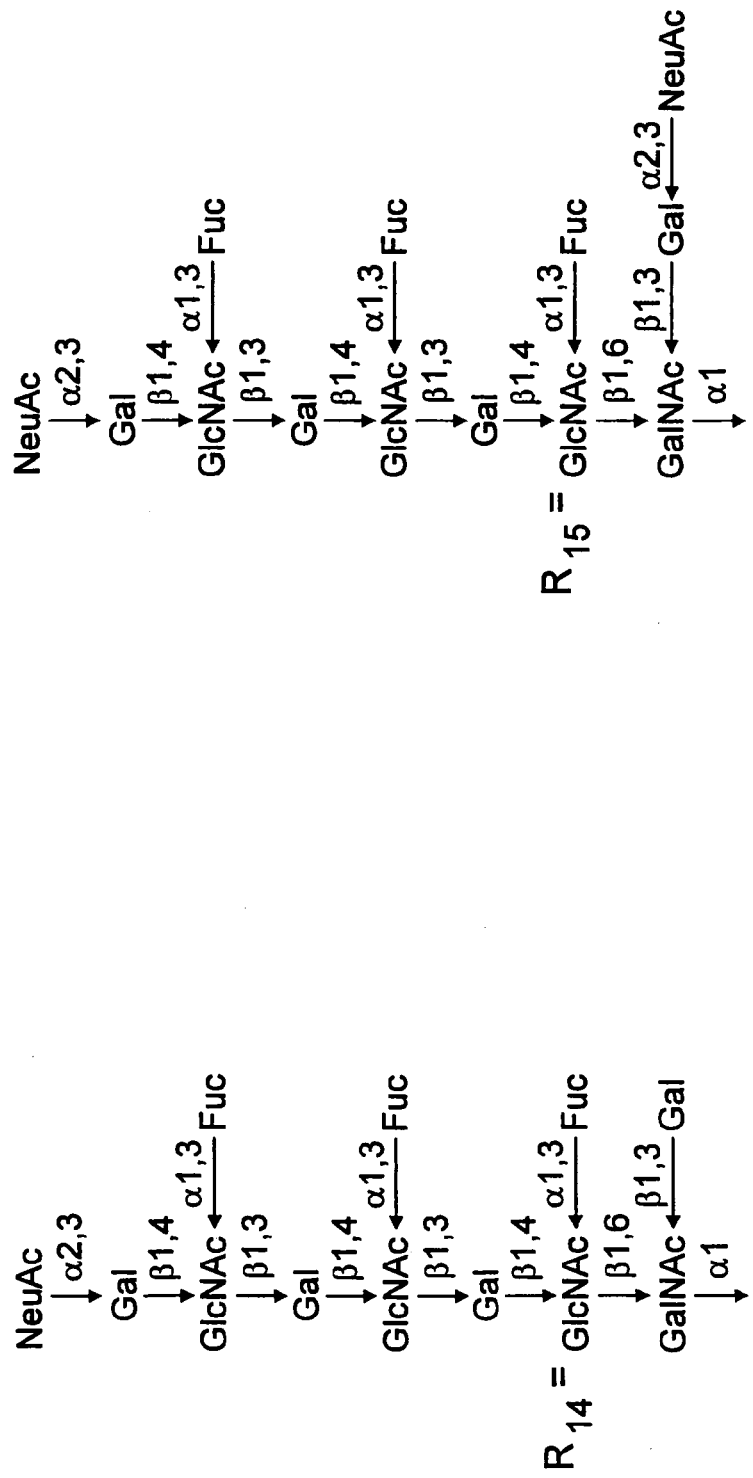
Figure 6:
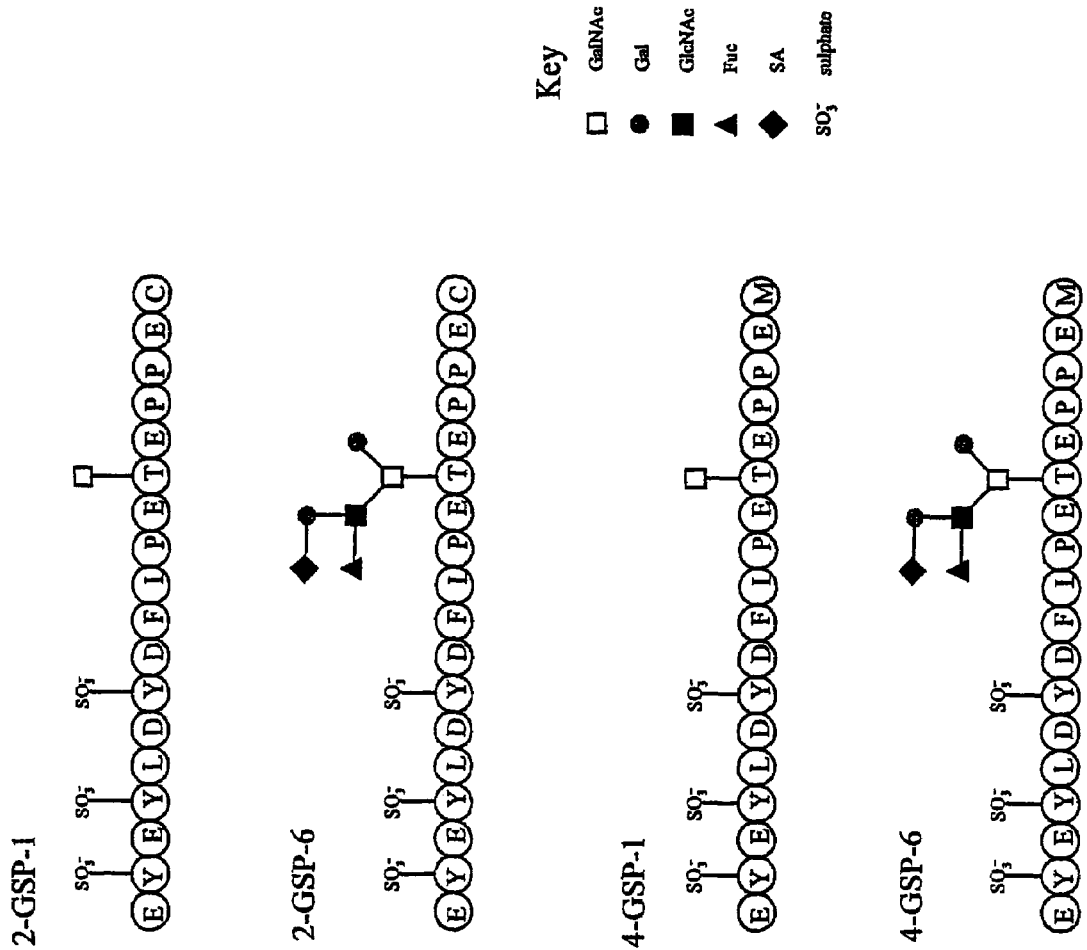
FIG. 6 shows four glycosulfopeptides synthesized for further analysis.

Examples of various oligosaccharides which may comprise the glycan R groups of the glycosulfopeptides contemplated for use herein are shown in FIGS. 5A, 5B and 5C. Methods of forming glycosulfopeptides having these glycans are shown in U.S. Ser. No. 09/334,013 which has been expressly incorporated herein by reference in its entirety. $R_1$ shown in FIG. 5A is the O-glycan of 2-GSP-6 and 4-GSP-6 shown in FIG. 6.

$R_2$ is like $R_1$ except a NeuAc (N-acetylneuraminic acid) group has been added in an α2,3 linkage via α2,3-ST (α2,3-sialyltransferase) in the presence of CMPNeuAc (cystosine monophosphate N-acetylneuraminic acid) to the Gal (galactose) linked to the GalNAc (N-acetylgalactosamine).

$R_3$ is like $R_1$ except the Gal has been linked to the GlcNAc (N-acetylglucosamine) in a β1,3 linkage via β1,3-GalT (β1,3-Galactosyltransferase) and Fuc (fucose) has been linked to the GlcNAc in an α1,4 linkage via α1,4-FT (α1,4-Fucosyltransferase).

$R_4$ is like $R_3$ except a NeuAc group has been added in an α2,3 linkage via α2,3-ST in the presence of CMPNeuAc to the Gal linked to the GalNAc.

$R_5$, $R_6$, $R_7$ and $R_8$ are like $R_1$, $R_2$, $R_3$, and $R_4$, respectively, except a sulfate group has been linked to the GlcNAc.

$R_9$ and $R_{11}$ are like $R_1$ and $R_7$, respectively, except they are lacking a Gal in β1,3 linkage to the GalNAc.

$R_{10}$ is like $R_9$ but has a sulfate group linked to the GlcNAc.

$R_{12}$ is like $R_1$ but has a sialyl Lewis$^x$ group in β1,3 linkage to the terminal Gal group.

$R_{13}$ is like $R_{12}$ but has a NeuAc in α2,3 linkage to the Gal linked to the GalNAc.

$R_{14}$ is like $R_{12}$ except the terminal NeuAc is replaced with a sialyl Lewis$^x$ group in β1,3 linkage to the terminal Gal group.

$R_{15}$ is like $R_{14}$ but has a NeuAc in α2,3 linkage to the Gal linked to the GalNAc.

Groups $R_1$–$R_{15}$ are merely examples of glycans which may form portions of the glycosulfopeptide contemplated herein. It will be understood, by a person of ordinary skill in the art, that these R groups are only representative of the many glycans which may constitute the glycan portion of the glycosulfopeptides of the present invention.

The glycosulfopeptide of present invention in its most basic form comprises a dipeptide comprising a sulfate group linked to a first amino acid of the dipeptide and a glycan linked to a second amino acid, wherein the glycan is a sialyl Lewis$^x$ group or comprises a sialyl Lewis$^x$ group as a portion thereof. Preferably, the glycan is O-linked to the peptide. The first amino acid, to which the sulfate is attached, is tyrosine (Tyr). The second amino acid, to which the O-glycan is linked, is preferably a threonine (Thr) or serine (Ser) residue but may be any other amino acid residue to which an glycan can be linked in O-linkage (for example, tyrosine, hydroxyproline or hydroxylysine).

Figure 1B:
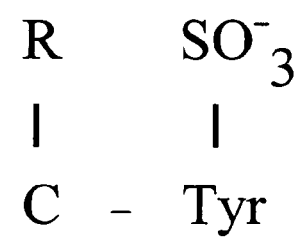

The present invention further contemplates that the glycan may be linked in N- or S-linkage to the peptide via an amino acid such as aspartic acid, asparagine, glutamic acid, glutamine, arginine, lysine, cysteine or methionine. The present invention contemplates that the peptide may be covalently derivatized to contain the glycan. Examples of such dipeptides defined herein are shown as formulas in FIGS. 1A and 1B wherein "C" represents a threonine, serine, or other residue to which the glycan may be linked, and R represents any one of the groups $R_1$–$R_{15}$ defined herein (and shown in FIGS. 5A–5C, for example). R, of course, may be another glycan not shown in FIGS. 5A–5C if it enables the glycosulfopeptides to function in accordance with the present invention, i.e., to bind with high affinity to P-selectin and inhibit leukocyte rolling.

Figure 2A:
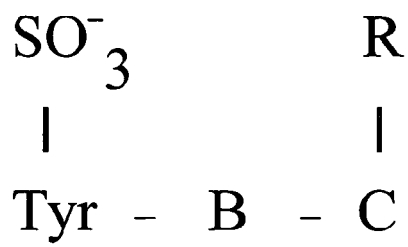
FIGS. 2A and 2B show formulas of alternative embodiments of glycosulfopeptides contemplated by the present invention wherein the R groups are those represented in FIGS. 5A–5C.
Figure 2B:
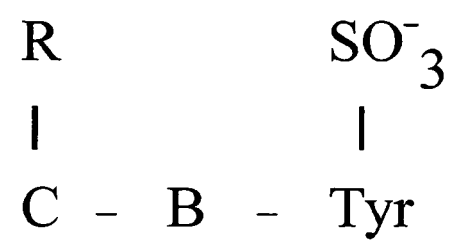

The present invention further contemplates peptides such as those represented as formulas in FIGS. 2A and 2B. Glycosulfopeptides in FIGS. 2A and 2B are similar to the glycosulfopeptides represented in FIGS. 1A and 1B except one or more amino acid residues represented by sequence "B" are positioned between the sulfate-linked residue (tyrosine) and the glycan linked residue "C" (i.e., Ser, Thr or other O-, N-, or S-linkable residue, natural or derivatized). Sequence B represents any amino acid and k in a preferred embodiment, can number from 0–12 amino acid residues. Where B=0, the peptides are those shown in FIGS. 1A and 1B above. Where B=2 or more amino acid residues, the 2 or more residues which comprise sequence B may be the same amino acid or different amino acids.

In one embodiment shown below, the glycosulfopeptide comprises a structure I which comprises a heptapeptide structure having a sulfated tyrosine residue near the N-terminal end and an O-glycosylated linking residue (such as Thr or Ser) near the C-terminal end of the peptide. This GSP comprises five intermediate amino acids represented as $X_1$, $X_2$, $X_3$, $X_4$, and $X_5$ as shown below. In one embodiment, $X_1$ is aspartic acid, $X_2$ is phenylalanine, $X_3$ is leucine, $X_4$ is proline and $X_5$ is glutamic acid. The heptapeptide may comprise a component (an amino acid or glycosyl component) which distinguishes it from a fragment of naturally-occurring or recombinantly expressed forms of PSGL-1, i.e., a fragment which could not be obtained from fragmentation of PSGL-1. Alternatively, the GSP may comprise fewer than seven amino acids wherein one or more of $X_1$–$X_5$ of structure I is not present. Alternatively, any one or more of $X_1$–$X_5$ may be substituted with a different amino acid, preferably one which has similar functional characteristics as the amino acid being substituted for. Alternatively, $X_1$–$X_5$ may comprise repeats of the same amino acid, e.g., five glycine residues. In an especially preferred version, the peptide contains one proline residue in the position between tyrosine and the O-linking residue to which the glycan is linked. In structure I, the O-glycan is $R_1$ of FIG. 5A.

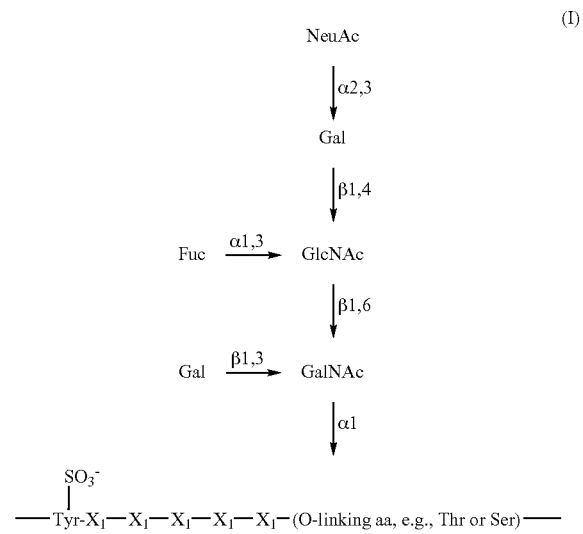

(I)

Figure 3A:
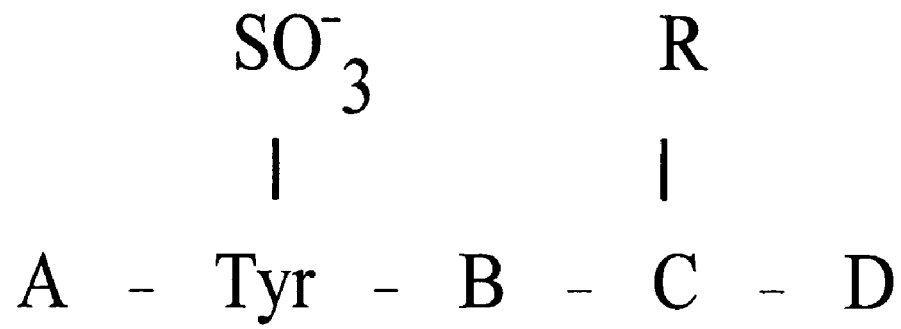
FIGS. 3A and 3B show formulas of additional alternative embodiments of glycosulfopeptides contemplated by the present invention wherein the R groups represented are those in FIGS. 5A–5C.
Figure 3B:
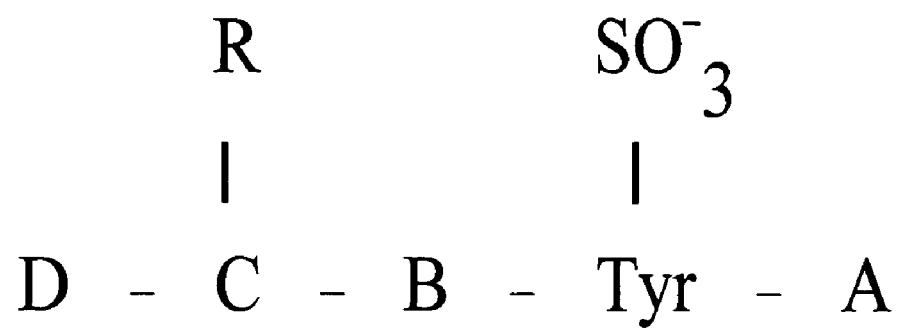

The glycosulfopeptides represented by formulas in FIGS. 3A and 3B are essentially the same as glycosulfopeptides in FIGS. 2A and 2B except each glycosulfopeptide has been extended in an N-terminal and/or C-terminal direction with additional amino acid residues "A" and/or "D", respectively, where sequence A and sequence D may be, in a preferred version of the invention, from 0–12 amino acids, and where each sequence A and sequence D may comprise any amino acid, preferably any natural amino acid. For example, A and D may each comprise one or more amino acids which are the same, or may comprise different amino acids, preferably any natural amino acid.

Figure 4A:
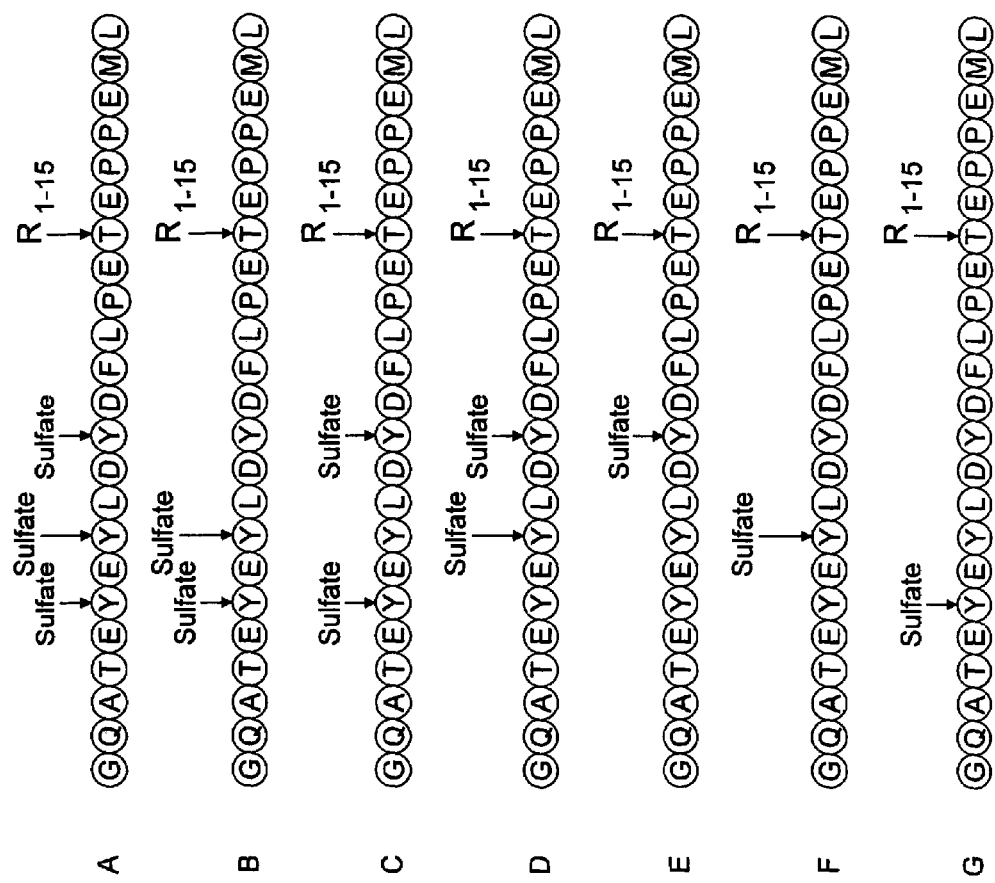
FIGS. 4A and 4B shows specific amino acid sequences for a number of exemplary glycosulfopeptides contemplated herein, wherein the glycosulfopeptides may comprise from one to three sulfates and R groups $R_1$–$R_{15}$ as defined in FIGS. 5A–5C.
Figure 4B:
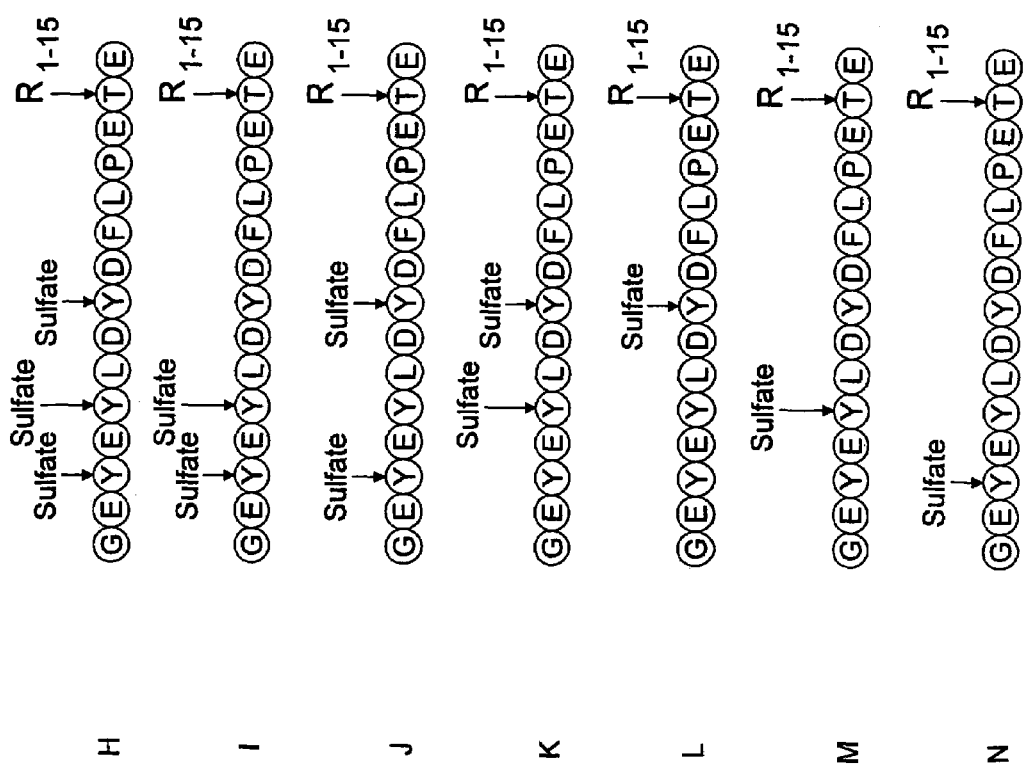

Further, it is contemplated herein that the glycosulfopeptides preferably comprise more than one sulfated tyrosine residue as shown in FIGS. 4A and 4B. FIGS. 4A and 4B show a number of preferred glycosulfopeptides A–N, each having one, two, or three sulfated tyrosine residues. Glycosulfopeptides with three sulfated tyrosines are especially preferred although GSPs having more than three sulfated tyrosines, for example 4 or 5, are also contemplated herein. Glycosulfopeptides A and H, for example, comprise three tyrosine residues each having a sulfate group linked thereto. Glycosulfopeptides B, C, D, I, J, and K each have two sulfated tyrosine residues. Glycosulfopeptides E, F, G, L, M, and N, each have one sulfated tyrosine group. The glycosulfopeptides represented in FIGS. 4A and 4B are intended to represent only a subset of the compounds contemplated herein as will be appreciated by a person of ordinary skill in the art and may be truncated to have more or fewer amino acid residues or may have substituted amino acids as described elsewhere herein, or may have more amino acids as described elsewhere herein (for example as shown below in Table II).

Preferably, the glycosulfopeptide comprises an O-glycan comprising a β1,6 linkage to GalNAc. In a particularly preferred embodiment of the present invention, the O-glycan of the glycosulfopeptide is core-2 based.

In particular, the methods of the present invention contemplate treating subjects with glycosulfopeptides having a structure II:

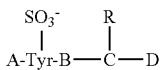

wherein:
Tyr is a tyrosine residue;
$SO_3^-$ is a sulfate group attached to the tyrosine residue;
C is an N-, S-, or O-linking amino acid residue;
R is a sialylated, fucosylated, N-acetyllactosaminoglycan in O-, S- or N- linkage to C (for example, one of $R_1-R_{15}$);
A, B, and D represent amino acid sequences each comprising from 0 to 12 amino acids, with the proviso that the compound comprises no more than 38 amino acids.

More particularly, A may comprise one or two sulfated tyrosine residues, or B may comprise one or two sulfated tyrosines. The glycosulfopeptide may have at least one additional sialylated, fucosylated O-, N-, or S-glycan linked to an amino acid residue. The "C" amino acid may be an O-linking amino acid, for example, serine, threonine, hydroxyproline, tyrosine, hydroxylysine, or an N-linking amino acid (e.g., asparagine, lysine, or glutamine) or an S-linking amino acid (such as methionine or cysteine). The R may comprise a β1,6 linkage to a GalNAc. The R group may be core-2 based. A Gal of the glycan may have been linked to the GalNAc via a core-1 β1,3-GalT (core-1 β1,3-Galactosyltransferase). The glycan may have a sialic acid which is neuraminic acid. The glycan may have a GlcNAc which is linked to the GalNAc via a β1,6 linkage.

Although N-acetyl neuraminic acid is the preferred sialic acid to be used, other sialic acids which function in a similar manner are contemplated to be used in the glycosulfopeptides claimed herein. These alternative sialic acids include those which can be transferred via the enzyme α2,3-ST, including N-glycolylneuraminic acid, N-acetylneuraminic acid, 9-0-acetyl-N-glycolylneuraminic acid, 9-0-acetyl-N-acetylneuraminic acid and other sialic acids described in Varki et al., "Sialic Acids As Ligands In Recognition Phenomena", *FASEB Journal,* 11(4):248–55, 1997, which is hereby incorporated by reference herein.

The peptide portion of the glycosulfopeptide preferably comprises from two amino acid residues to 30 amino acid residues, and more particularly may comprise from 3 to 29 amino acid residues, 4 to 28 amino acid residues, 5 to 27 amino acid residues, 6 to 26 amino acid residues, 7 to 25 amino acid residues, 8 to 24 amino acid residues, 9 to 23 amino acid residues, 10 to 22 amino acid residues, 11 to 21 amino acid residues, 12 to 20 amino acid residues, 13 to 19 amino acid residues, 14 to 18 amino acid residues, 15 to 17 amino acid residues, or 16 amino acid residues.

The invention further contemplates a method of using a glycosulfopeptide comprising a structure III:

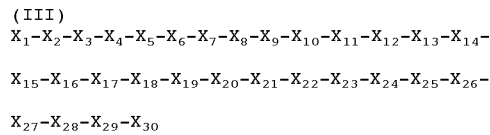

wherein:
$X_1$ is ala, cys, asp, glu, phe, gly, his, ile, lys, leu, met, asn, pro, gln, arg, ser, thr, val, trp, or tyr, or is absent;
$X_2$ is ala, cys, asp, glu, phe, gly, his, ile, lys, leu, met, asn, pro, gln, arg, ser, thr, val, trp, or tyr, or is absent;
$X_3$ is ala, cys, asp, glu, phe, gly, his, ile, lys, leu, met, asn, pro, gln, arg, ser, thr, val, trp, or tyr, or is absent;
$X_4$ is ala, cys, asp, glu, phe, gly, his, ile, lys, leu, met, asn, pro, gln, arg, ser, thr, val, trp, or tyr, or is absent;
$X_5$ is ala, cys, asp, glu, phe, gly, his, ile, lys, leu, met, asn, pro, gln, arg, ser, thr, val, trp, or tyr, or is absent;
$X_6$ is ala, cys, asp, glu, phe, gly, his, ile, lys, leu, met, asn, pro, gln, arg, ser, thr, val, trp, or tyr, or is absent;
$X_7$ is ala, cys, asp, glu, phe, gly, his, ile, lys, leu, met, asn, pro, gln, arg, ser, thr, val, trp, or tyr, or is absent;
$X_8$ is ala, cys, asp, glu, phe, gly, his, ile, lys, leu, met, asn, pro, gln, arg, ser, thr, val, trp, or tyr; or is absent;
$X_9$ is a sulfated tyr;
$X_{10}$ is ala, cys, asp, glu, phe, gly, his, ile, lys, leu, met, asn, pro, gln, arg, ser, thr, val, trp, or tyr;
$X_{11}$ is a sulfated tyr;
$X_{12}$ is ala, cys, asp, glu, phe, gly, his, ile, lys, leu, met, asn, pro, gln, arg, ser, thr, val, trp, or tyr;
$X_{13}$ is ala, cys, asp, glu, phe, gly, his, ile, lys, leu, met, asn, pro, gln, arg, ser, thr, val, trp, or tyr, or is absent;
$X_{14}$ is a sulfated tyr;
$X_{15}$ is ala, cys, asp, glu, phe, gly, his, ile, lys, leu, met, asn, pro, gln, arg, ser, thr, val, trp, or tyr, or is absent;
$X_{16}$ is ala, cys, asp, glu, phe, gly, his, ile, lys, leu, met, asn, pro, gln, arg, ser, thr, val, trp, or tyr, or is absent;
$X_{17}$ is ala, cys, asp, glu, phe, gly, his, ile, lys, leu, met, asn, pro, gln, arg, ser, thr, val, trp, or tyr, or is absent;
$X_{18}$ is ala, cys, asp, glu, phe, gly, his, ile, lys, leu, met, asn, pro, gln, arg, ser, thr, val, trp, or tyr, or is absent;
$X_{19}$ is ala, cys, asp, glu, phe, gly, his, ile, lys, leu, met, asn, pro, gln, arg, ser, thr, val, trp, or tyr;
$X_{20}$ is a thr, ser, hydroxyproline, tyr, met, hydroxylysine, lys, cys, asn, or gln having a glycan linked thereto, the glycan comprising a sialyl Lewis$^x$ or sialyl Lewis$^a$ group such as, for example, any one of the R groups defined elsewhere herein;
$X_{21}$ is ala, cys, asp, glu, phe, gly, his, ile, lys, leu, met, asn, pro, gln, arg, ser, thr, val, trp, or tyr, or is absent;
$X_{22}$ is ala, cys, asp, glu, phe, gly, his, ile, lys, leu, met, asn, pro, gln, arg, ser, thr, val, trp, or tyr, or is absent;
$X_{23}$ ala, cys, asp, glu, phe, gly, his, ile, lys, leu, met, asn, pro, gln, arg, ser, thr, val, trp, or tyr, or is absent;
$X_{24}$ ala, cys, asp, glu, phe, gly, his, ile, lys, leu, met, asn, pro, gln, arg, ser, thr, val, trp, or tyr, or is absent;
$X_{25}$ ala, cys, asp, glu, phe, gly, his, ile, lys, leu, met, asn, pro, gln, arg, ser, thr, val, trp, or tyr, or is absent;
$X_{26}$ ala, cys, asp, glu, phe, gly, his, ile, lys, leu, met, asn, pro, gln, arg, ser, thr, val, trp, or tyr, or is absent;
$X_{27}$ ala, cys, asp, glu, phe, gly, his, ile, lys, leu, met, asn, pro, gln, arg, ser, thr, val, trp, or tyr, or is absent;
$X_{28}$ ala, cys, asp, glu, phe, gly, his, ile, lys, leu, met, asn, pro, gln, arg, ser, thr, val, trp, or tyr, or is absent;
$X_{29}$ ala, cys, asp, glu, phe, gly, his, ile, lys, leu, met, asn, pro, gln, arg, ser, thr, val, trp, or tyr, or is absent;
$X_{30}$ ala, cys, asp, glu, phe, gly, his, ile, lys, leu, met, asn, pro, gln, arg, ser, thr, val, trp, or tyr, or is absent;
and wherein the glycosulfopeptide has leukocyte rolling inhibiting activity.

The present invention more particularly comprises a method of using a glycosulfopeptide comprising a structure IV:

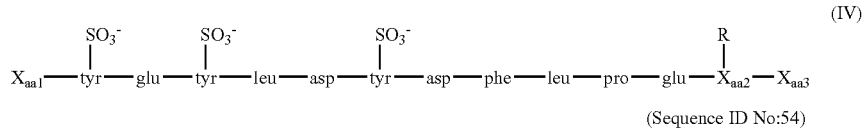

(Sequence ID No:54)

wherein $X_{aa1}$ an amino acid selected from the group comprising ala, cys, asp, glu, phe, gly, his, ile, lys, leu, met, asn, pro, gln, arg, ser, thr, val, trp, or tyr, or is absent;

$X_{aa2}$ is thr, ser, tyr, met, asn, gln, cys, lys, hydroxyproline, or hydroxylysine, or any N-linking, S-linking or O-linking amino acid;

R is a sialylated, fucosylated, N-acetyllactosaminoglycan in N-, S- or O-linkage to $X_{aa2}$; and $X_{aa3}$ is an acid selected from the group comprising ala, cys, asp, glu, phe, gly, his, ile, lys, leu, met, asn, pro, gln, arg, ser, thr, val, trp, or tyr, or is absent.

Where used herein, a GSP comprising structure IV is intended to mean any GSP having 38 or fewer amino acids which includes structure IV in whole or in part.

The present invention more particularly comprises a method of using a glycosulfopeptide comprising a structure V:

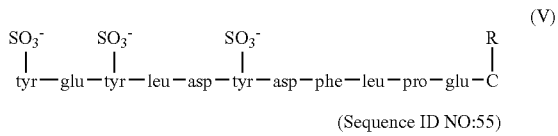

(Sequence ID NO:55)

wherein C is thr, ser, tyr, met, asn, gln, cys, lys, hydroxyproline, or hydroxylysine, or any N-linking, S-linking or O-linking amino acid; and R is a sialylated, fucosylated, N-acetyllactosaminoglycan in N-, S- or O-linkage to C.

Where used herein, a GSP comprising structure V is intended to mean any GSP having 38 or fewer amino acids which includes structure V in whole or in part, including additional amino acids upstream of the N-terminal tyrosine or downstream of the C-terminal "C" amino acid.

The present invention more particularly comprises a conjugated glycosulfopeptide and method of its use, the conjugated glycosulfopeptide comprising a structure VI:

and a PEG polymer carrier comprising at least one polyalkylene glycol molecule and a X linking group which conjugates the glycosulfopeptide to the PEG molecule, the linking group comprising at least one amino acid selected from the group comprising ala, cys, asp, glu, phe, gly, his, ile, lys, leu, met, asn, pro, gln, arg, ser, thr, val, trp, or tyr; and wherein $X_{aa1}$ of VI is thr, ser, tyr, met, cys, asn, gln, lys, hydroxyproline, or hydroxylysine or any N-linking, S-linking or O-linking amino acid; and $X_{aa2}$ of VI is an amino acid selected from the group comprising ala, cys, asp, glu, phe, gly, his, ile, lys, leu, met, asn, pro, gln, arg, ser, thr, val, trp, or tyr, or is absent.

Another X linking group or amino acid could be positioned at another site within the peptide backbone of the glycosulfopeptide. The PEG polymeric carrier may further comprise one or more additional amino acid groups in linkage to the GSP.

It will be noted that generally the specific amino acids which make up the peptide backbones of the GSPs described herein (e.g., structures I–VI) can be substituted with other natural amino acids (except the sulfated tyrosine and R-linking amino acids). Structure VI may comprise from 1 to 12 amino acids disposed between the PEG and the N-terminalmost sulfated tyrosine.

More particular, amino acids are substituted with other amino acids from the same class. These are referred to as "conservative substitutions".

By "conservative substitution" is meant the substitution of an amino acid by another one of the same class; the classes according to Table I.

TABLE I

| CLASS | AMINO ACID |
|---|---|
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His |

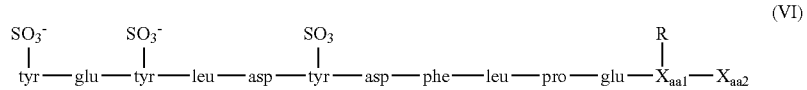

(VI)

(Sequence ID NO:56)

Non-conservative substitutions (outside each class of Table I) may be made as long as these do not entirely destroy the effectiveness of the glycosulfopeptide.

The glycosulfopeptides contemplated herein may be produced recombinantly in an expression system comprising a host cell which has been transformed to contain a nucleic acid encoding the peptide backbone of the glycosulfopeptide and nucleic acids encoding the enzymes necessary for expression of the GSP. Transformed host cells such as eukaryotic cells can be cultured to produce the GSPs. The GSPs can be made synthetically using methods shown in U.S. Ser. No. 09/334,013, which has been expressly incorporated by reference herein.

The invention includes glycosulfopeptide structures presented in Table II (SEQ ID NO. 15–48). Each of the amino acids except the sulfated tyrosine (represented as Styr) and glycosylated threonine (represented as Rthr) may be substituted with any other amino acid, but preferably with an amino acid from within its own class as shown in Table I. The threonine which is glycosylated (Rthr) may be substituted by serine, tyrosine, hydroxyproline, hydroxylysine, methionine, cysteine, lysine, asparagine, or glutamine, for example.

TABLE II

Table II. Examples of glycosulfopeptides. "Styr" represents sulfated tyrosine; "Rthr" represents a threonine having a glycan linked thereto.

(SEQ ID NO: 15)
gln-ala-thr-glu-Styr-glu-Styr-leu-asp-Styr-asp-phe-leu-pro-glu-Rthr-glu-pro-pro-glu-met-leu (SEQ ID NO: 16)
ala-thr-glu-Styr-glu-Styr-leu-asp-Styr-asp-phe-leu-pro-glu-Rthr-glu-pro-pro-glu-met-leu (SEQ ID NO: 17)
gln-ala-thr-glu-Styr-glu-Styr-leu-asp-Styr-asp-phe-leu-pro-glu-Rthr-glu-pro-pro-glu-met (SEQ ID NO: 18)
thr-glu-Styr-glu-Styr-leu-asp-Styr-asp-phe-leu-pro-glu-Rthr-glu-pro-pro-glu-met-leu (SEQ ID NO: 19)
gln-ala-thr-glu-Styr-glu-Styr-leu-asp-Styr-asp-phe-leu-pro-glu-Rthr-glu-pro-pro-glu (SEQ ID NO: 20)
glu-Styr-glu-Styr-leu-asp-Styr-asp-phe-leu-pro-glu-Rthr-glu-pro-pro-glu-met-leu (SEQ ID NO: 21)
gln-ala-thr-glu-Styr-glu-Styr-leu-asp-Styr-asp-phe-leu-pro-glu-Rthr-glu-pro-pro (SEQ ID NO: 22)
Styr-glu-Styr-leu-asp-Styr-asp-phe-leu-pro-glu-Rthr-glu-pro-pro-glu-met-leu (SEQ ID NO: 23)
gln-ala-thr-glu-Styr-glu-Styr-leu-asp-Styr-asp-phe-leu-pro-glu-Rthr-glu-pro (SEQ ID NO: 24)
gln-ala-thr-glu-Styr-glu-Styr-leu-asp-Styr-asp-phe-leu-pro-glu-Rthr-glu (SEQ ID NO: 25)
ala-thr-glu-Styr-glu-Styr-leu-asp-Styr-asp-phe-leu-pro-glu-Rthr-glu-pro-pro-glu-met (SEQ ID NO: 26)
thr-glu-Styr-glu-Styr-leu-asp-Styr-asp-phe-leu-pro-glu-Rthr-glu-pro-pro-glu-met TABLE II-continued Table II. Examples of glycosulfopeptides. "Styr" represents sulfated tyrosine; "Rthr" represents a threonine having a glycan linked thereto.

(SEQ ID NO: 27)
glu-Styr-glu-Styr-leu-asp-Styr-asp-phe-leu-pro-glu-Rthr-glu-pro-pro-glu-met (SEQ ID NO: 28)
Styr-glu-Styr-leu-asp-Styr-asp-phe-leu-pro-glu-Rthr-glu-pro-pro-glu-met (SEQ ID NO: 29)
ala-thr-glu-Styr-glu-Styr-leu-asp-Styr-asp-phe-leu-pro-glu-Rthr-glu-pro-pro-glu (SEQ ID NO: 30)
thr-glu-Styr-glu-Styr-leu-asp-Styr-asp-phe-leu-pro-glu-Rthr-glu-pro-pro-glu (SEQ ID NO: 31)
glu-Styr-glu-Styr-leu-asp-Styr-asp-phe-leu-pro-glu-Rthr-glu-pro-pro-glu (SEQ ID NO: 32)
Styr-glu-Styr-leu-asp-Styr-asp-phe-leu-pro-glu-Rthr-glu-pro-pro-glu (SEQ ID NO: 33)
ala-thr-glu-Styr-glu-Styr-leu-asp-Styr-asp-phe-leu-pro-glu-Rthr-glu-pro-pro (SEQ ID NO: 34)
thr-glu-Styr-glu-Styr-leu-asp-Styr-asp-phe-leu-pro-glu-Rthr-glu-pro-pro (SEQ ID NO: 35)
glu-Styr-glu-Styr-leu-asp-Styr-asp-phe-leu-pro-glu-Rthr-glu-pro-pro (SEQ ID NO: 36)
Styr-glu-Styr-leu-asp-Styr-asp-phe-leu-pro-glu-Rthr-glu-pro-pro (SEQ ID NO: 37)
ala-thr-glu-Styr-glu-Styr-leu-asp-Styr-asp-phe-leu-pro-glu-Rthr-glu-pro (SEQ ID NO: 38)
thr-glu-Styr-glu-Styr-leu-asp-Styr-asp-phe-leu-pro-glu-Rthr-glu-pro (SEQ ID NO: 39)
glu-Styr-glu-Styr-leu-asp-Styr-asp-phe-leu-pro-glu-Rthr-glu-pro (SEQ ID NO: 40)
Styr-glu-Styr-leu-asp-Styr-asp-phe-leu-pro-glu-Rthr-glu-pro (SEQ ID NO: 41)
ala-thr-glu-Styr-glu-Styr-leu-asp-Styr-asp-phe-leu-pro-glu-Rthr-glu (SEQ ID NO: 42)
thr-glu-Styr-glu-Styr-leu-asp-Styr-asp-phe-leu-pro-glu-Rthr-glu (SEQ ID NO: 43)

TABLE II-continued

Figure 7:
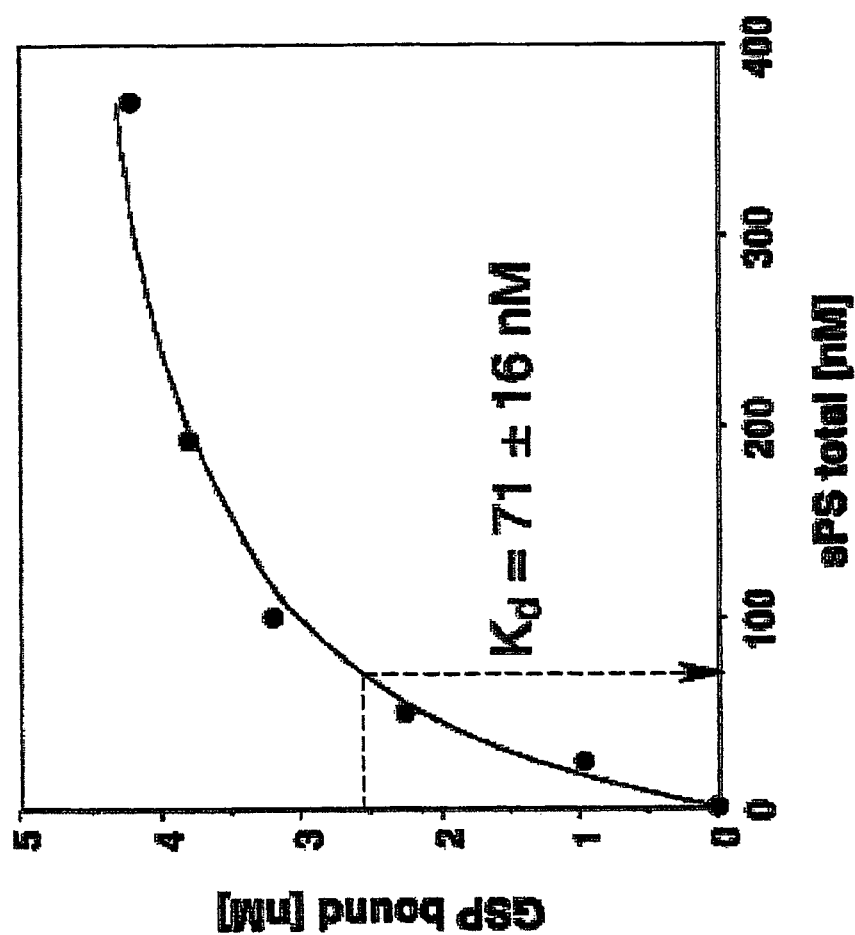
FIG. 7 is a graph showing equilibrium affinity binding of 4-GSP-6 to human P-selectin at low salt.

Table II. Examples of glycosulfopeptides. "Styr" represents sulfated tyrosine; "Rthr" represents a threonine having a glycan linked thereto.

glu-Styr-glu-Styr-leu-asp-Styr-asp-phe-leu-pro-glu-Rthr-glu (SEQ ID NO: 44)
Styr-glu-Styr-leu-asp-Styr-asp-phe-leu-pro-glu-Rthr-glu- (SEQ ID NO: 45)
ala-thr-glu-Styr-glu-Styr-leu-asp-Styr-asp-phe-leu-pro-glu-Rthr (SEQ ID NO: 46)
thr-glu-Styr-glu-Styr-leu-asp-Styr-asp-phe-leu-pro-glu-Rthr (SEQ ID NO: 47)
glu-Styr-glu-Styr-leu-asp-Styr-asp-phe-leu-pro-glu-Rthr (SEQ ID NO: 48)
Styr-glu-Styr-leu-asp-Styr-asp-phe-leu-pro-glu-Rthr Experimental A series of glycosulfopeptides (GSPs) were synthesized (FIG. 6). 2-GSP-1 (SEQ ID NO. 49) and 4-GSP-1(SEQ ID No. 51) each carried only N-acetylgalactosamine (GalNAc) on the threonine residue, and had cysteine and methionine as C-terminal amino acid residues, respectively. 2-GSP-6 (SEQ ID No. 50) and 4-GSP-6 (SEQ ID No. 52) were similar to 2-GSP-1 and 4-GSP-1, respectively, except each had an $R_1$ group in O-linkage to the threonine rather than a GalNAc. Positioning of a core-2 based O-glycan containing sLe$^x$ at a position near to locations of potential tyrosine sulfation is critical for high affinity binding. Although absence of sulfate at one or more of three tyrosines on the molecule had a lesser negative impact on binding than absence of sLe$^x$, optimal binding was seen only when each of all available tyrosines (e.g., three) were sulfated. Equilibrium binding affinity of 4-GSP-6 to human P-selectin in vitro at 50 mM NaCl was 71±16 nM (FIG. 7).

Experiments were conducted to determine whether derivatives of GSP-6 could compete with cell bound selectin ligands and modify leukocyte rolling in a physiological setting. Presented here are data which indicate that glycosulfopeptides 2-GSP-6 and 4-GSP-6 competitively inhibit leukocyte rolling in vivo and thus that these and other glycosulfopeptides have other therapeutic effects in vivo as described further herein below.

Methods and Results

Equilibrium Gel Filtration Chromatograpy

Hummel-Dreyer equilibrium gel filtration experiments were conducted as described. SEPHADEX G-100 columns were equilibrated with buffer and $^{35}SO_3$-4-GSP-6 (10,000 cpm/ml, specific activity 1700 cpm/pmol). Different amounts of soluble P-selectin were pre-incubated with buffer plus $^{35}SO_3$-4-GSP-6 and then added to the column. Samples were eluted with buffer plus $^{35}SO_3$-4-GSP-6 and 140 µl fractions were collected at a flow rate of 70 µl/min. Radioactivity was determined by liquid scintillation counting. Bound GSP and total soluble P-selectin were calculated from equilibrium gel filtration data by dividing the molar amounts of 4-GSP-6 and soluble P-selectin by the peak volume of GSP-soluble P-selectin complex.

Animals

C57BL/6 mice were purchased from Harlan (Oxon, UK). Male mice weighing between 25 and 35 g were used in these experiments. All procedures were approved by the University of Sheffield ethics committee and by the Home Office Animals (Scientific Procedures) Act 1985 of the UK.

Intravital Microscopy

The cremaster was prepared for intravital microscopy as described. Briefly, mice were anaesthetized with a mixture of ketamine, xylazine and atropine, cannulations of the trachea, jugular vein and carotid artery were performed, and the cremaster muscle exposed and spread over a specialized viewing platform. Temperature was controlled using a thermistor regulated heating pad (PDTRONICS, Sheffield, UK) and the cremaster was superfused with thermocontrolled (36° C.) bicarbonate buffered saline.

Microscopic observations were made using an upright microscope (NIKON ECLIPSE E600-FN, Nikon UK Ltd, UK) equipped with a water immersion objective (40x/0.80 W). Images were recorded using a CCD camera (DAGE MTI DC-330, DAGE MTI Inc, Michigan City, Ind.) onto sVHS video-cassettes. Venules (20–40 µM diameter) were selected and typically observed for the entire experimental period. Centre-line blood flow velocity ($V_{CL}$) in was measured in vessels of interest using a commercially available velocimeter (CIRCUSOFT, Hockessin, Del.). Vessels with $V_{CL}$ between 1 and 5 mm/s were selected for these studies.

Control leukocyte rolling was recorded exactly 30 min after exposure of the cremaster muscle for intravital microscopy since leukocyte rolling at this time is almost exclusively P-selectin-dependent. GSPs were injected at 31 min and their effects monitored for 10 min. As a positive control, the anti-P-selectin antibody RB40.34 (PHARMINGEN, Oxford, UK) was routinely injected at the end of experiments confirming that rolling was P-selectin dependent. Blood flow velocities and circulating leukocyte concentrations were measured at key times (before and after treatments) during experiments.

Distribution and Clearance of 4-GSP-6

4-GSP-6 was radioiodinated ($^{125}I$) using iodobeads according to manufacturer's (PIERCE, Rockford, Ill.) instructions giving specific activity of 5 mCi/µmol). A mixture of $^{125}I$-4-GSP-6 (1 µg) and unlabelled 4-GSP-6 were injected into mice by the jugular vein at a final dose of 4.3 µmol/kg. Blood samples (10 µl) were drawn 1, 2, 4 and 10 min after injection of material. Mice were then exsanguinated and urine drained from the bladder into a syringe. Bladder, kidneys, spleen, liver, heart, lungs and brain were also collected. Samples were counted on an automatic gamma counter (WALLAC 1470, EG&G, Berthold, Milton Keynes, UK) and cpm used to calculate % of injected material located in each of the studied fluids and organs. Total recovered urine and whole organs were counted along with samples of blood. The proportion of 4-GSP-6 remaining in the blood was calculated from sample counts assuming a total blood volume equivalent to 8% of body weight.

2-GSP-6 and 4-GSP-6 Competitively Inhibit P-Selectin-Dependent Leukocyte Rolling In Vivo.

Figure 8:
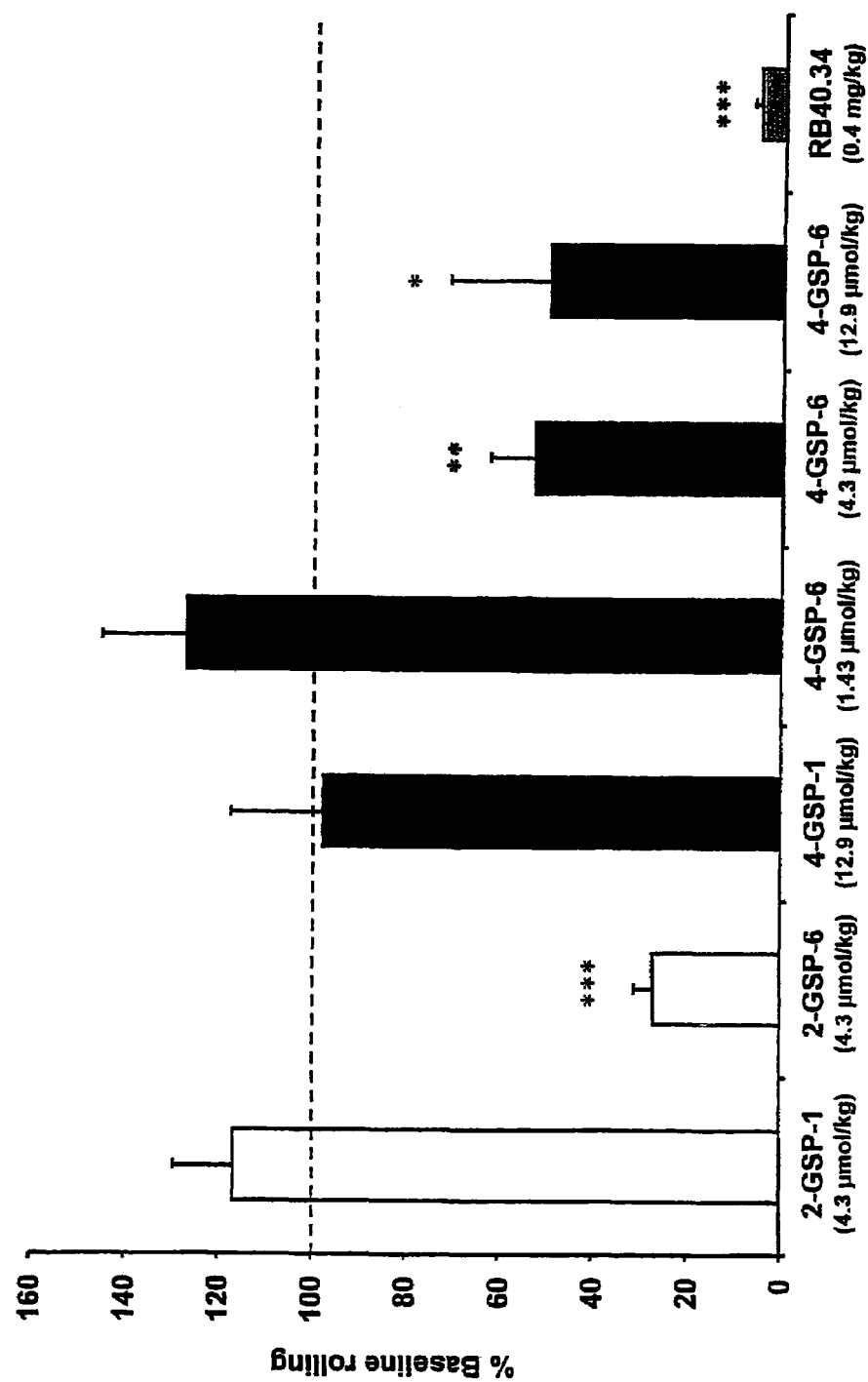
FIG. 8 shows the effects of several GSPs on leukocyte rolling in vivo.

2-GSP-6 and 4-GSP-6 were predicted to compete with cell bound P-selectin ligands and inhibit P-selectin-dependent leukocyte rolling in vivo. Intravital microscopy of the mouse cremaster muscle was used to investigate this potential. Surgical preparation of mice for intravital microscopy stimulated P-selectin dependent rolling as described. Baseline rolling was observed 30 min after surgery, and GSPs were injected at 31 min. Effects of GSPs on the number and velocity of rolling cells were determined from recordings taken between 32 and 42 min after surgery. Both 2-GSP-6 and 4-GSP-6 reduced pre-existing P-selectin dependent leukocyte rolling, whereas 2-GSP-1 and 4-GSP-1 did not (FIG. 8). These effects could not be attributed to changes in blood flow or circulating leukocyte counts since blood flow velocity remained stable throughout observation and systemic leukocyte counts increased slightly following treatment with either 2-GSP-6 or 4-GSP-6 (Table III).

TABLE III

Table III. Effects of 2-GSP-6 and 4-GSP-6 on circulating leukocyte count and blood flow in mice with P-selectin-dependent leukocyte rolling.

| TREATMENT | Systematic leukocytes (cells/µl blood) | | Centerline blood flow velocity (mm/sec) | |
|---|---|---|---|---|
| | 30 min | 32 min | 30 min | 32 min |
| 2-GSP-6 (4.3 µmol/kg) | 5840 ± 935 | 6360 ± 1108 | 3743 ± 493 | 3777 ± 495 |
| 4-GSP-6 (4.3 µmol/kg) | 4100 ± 300 | 8300 ± 1100 | 3865 ± 413 | 4067 ± 770 |

Interestingly, 2-GSP-6 inhibited P-selectin dependent rolling to a greater extent than 4-GSP-6 although neither compound matched the complete inhibition given by the P-selectin blocking antibody (RB40.34). This finding is similar to reported effects of anti-PSGL-1 antibodies, which also reduce P-selectin dependent leukocyte rolling substantially but not to the same extent as P-selectin blocking antibodies. The effects of 4-GSP-6 were dose-dependent and were maximal at 4.3 µmol/kg (FIG. 8).

Figure 9:
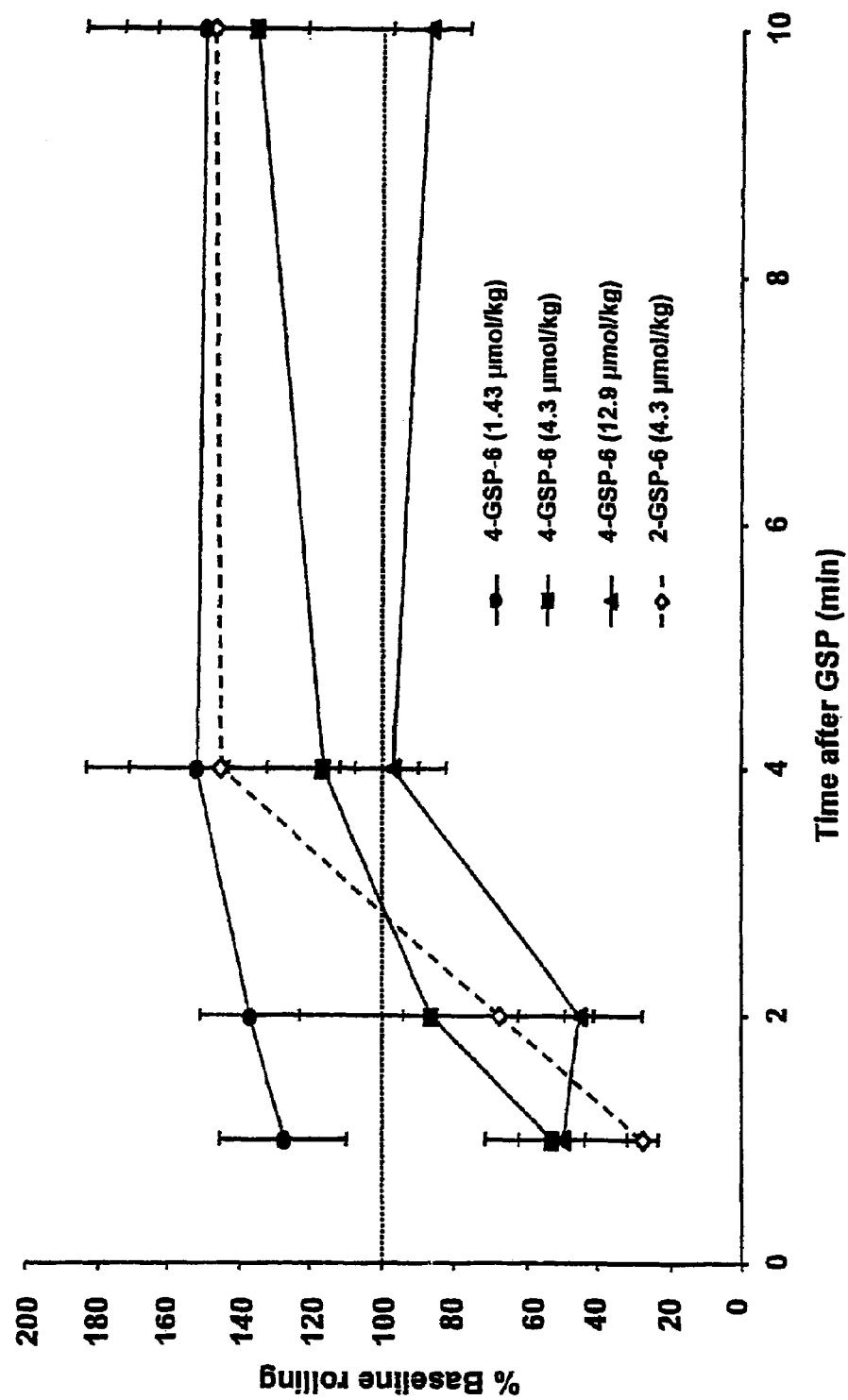
FIG. 9 shows the effects of 2-GSP-6 and 4-GSP-6 on leukocyte rolling over a ten minute period.
Figure 10:
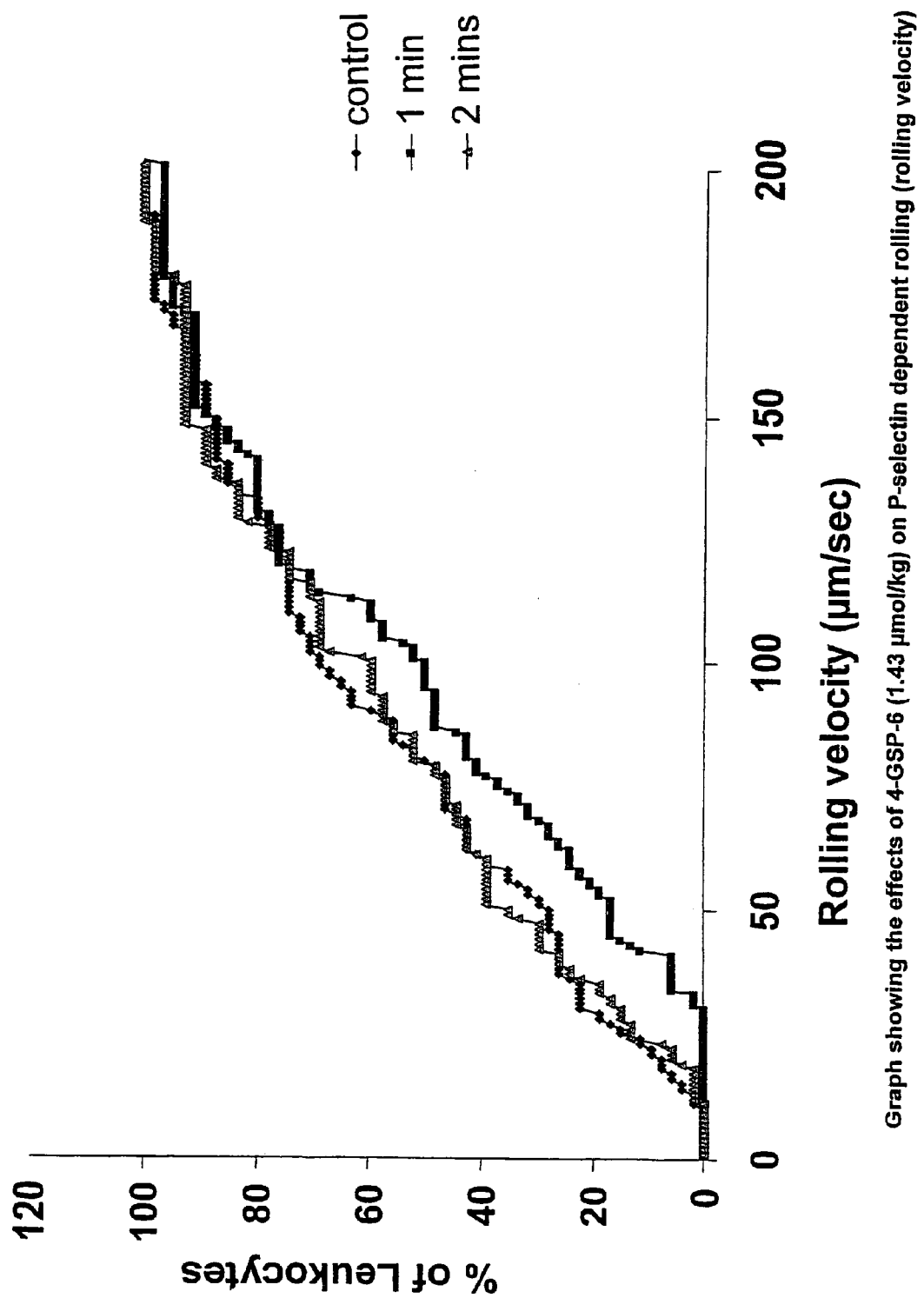
FIG. 10 shows the effects of 4-GSP-6 on leukocyte rolling velocity at a dose of 1.43 μmol/kg.
Figure 11:
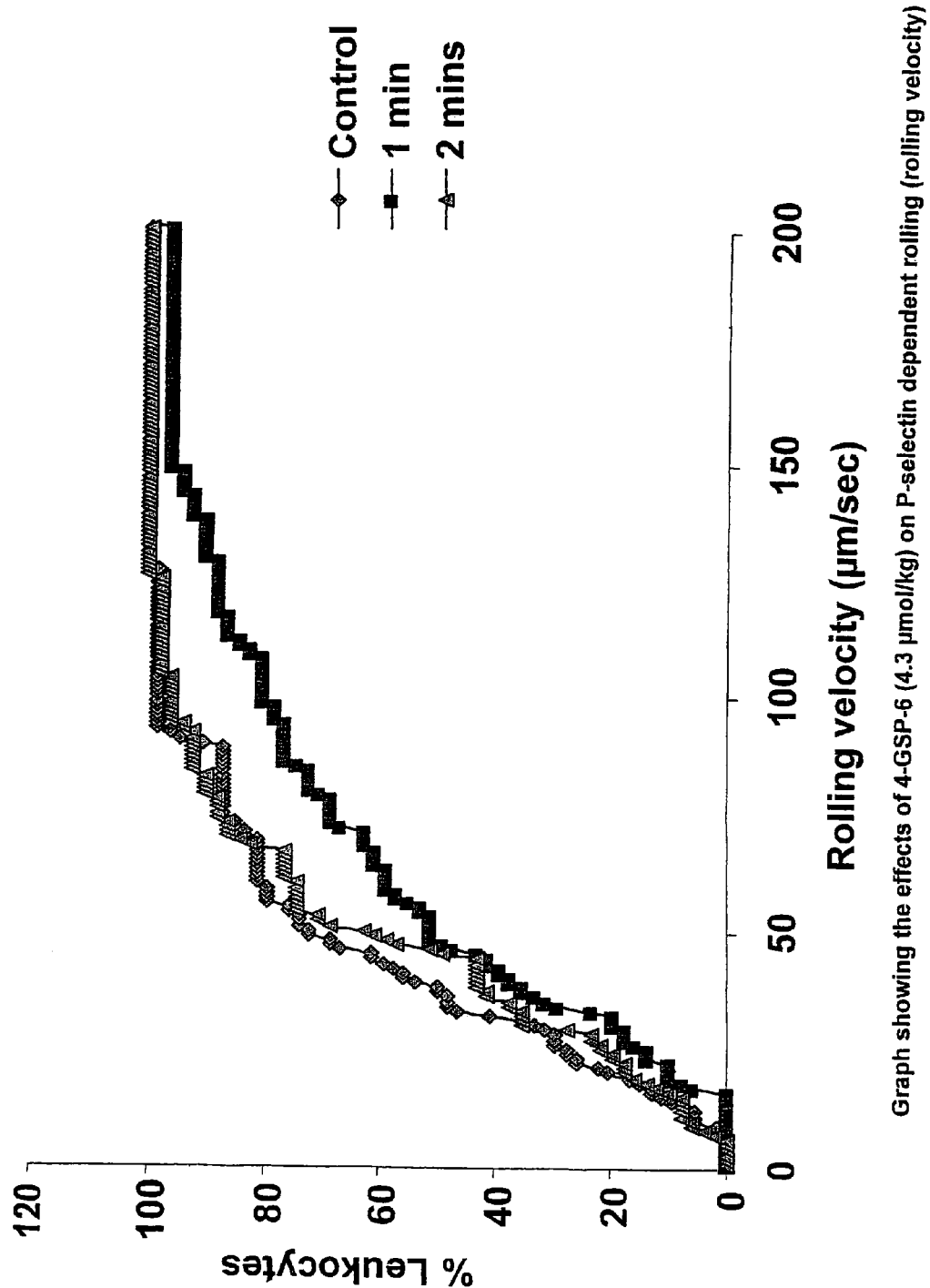
FIG. 11 shows the effects of 4-GSP-6 on leukocyte rolling velocity at a dose of 4.3 μmol/kg.
Figure 12:
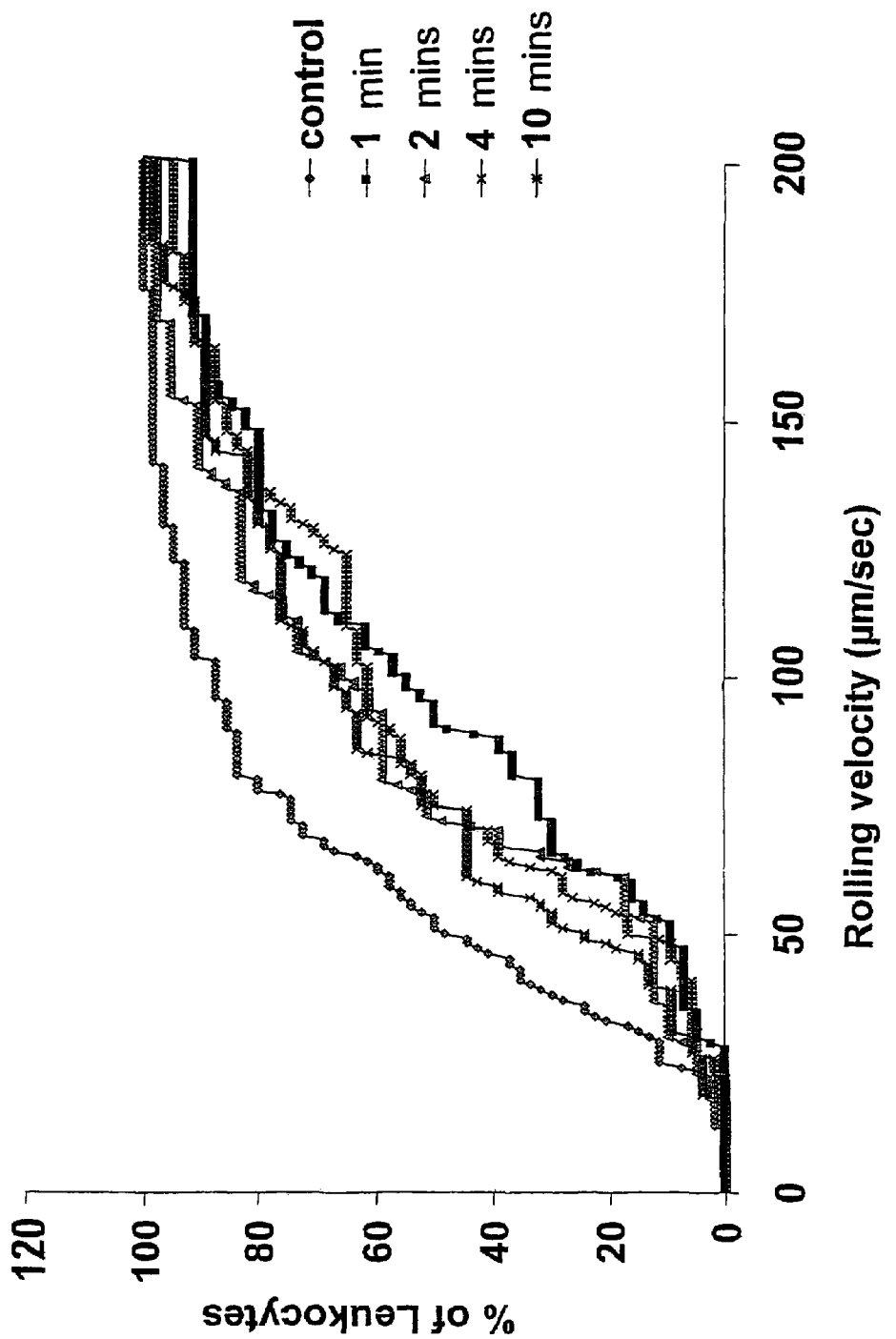
FIG. 12 shows the effects of 4-GSP-6 on leukocyte rolling velocity at a dose of 12.9 μmol/kg.

The effects of 2-GSP-6 and 4-GSP-6 were significant but short lived. 4-GSP-6 caused significant inhibition of leukocyte rolling 1-2 min after injection at 4.3 µmol/kg, but this effect was reversed within 2–3 min (FIG. 9). Application of a higher dose (12.9 µmol/kg) of 4-GSP-6 did not increase the magnitude of inhibition, but did slightly prolong the effect. In addition to reducing the number of cells rolling through a given vessel, selectin inhibitors can also increase the velocity of cells that continue to roll. Although 4-GSP-6 failed to reduce leukocyte rolling when given at 1.43 µmol/kg, this dose of the peptide did cause a significant increase in leukocyte rolling velocity 1 min after application as indicated by a shift to the right of the distribution (FIG. 10). This effect was reversed within 1 min. The increase in velocity caused by 4-GSP-6 at 4.3 µmol/kg was more convincing, but was similarly reversed within 1 min (FIG. 11). In contrast, application of 4-GSP-6 at 12.9 µmol/kg caused a sustained increase in leukocyte rolling velocity (FIG. 12). Since surgically-induced rolling develops from a purely P-selectin-dependent response to one that is dependent on both P- and L-selectins between 30 and 60 min, we did not study the duration of action of 4-GSP-6 beyond 10 min.

Rapid Clearance of 4-GSP-6

Figure 13:
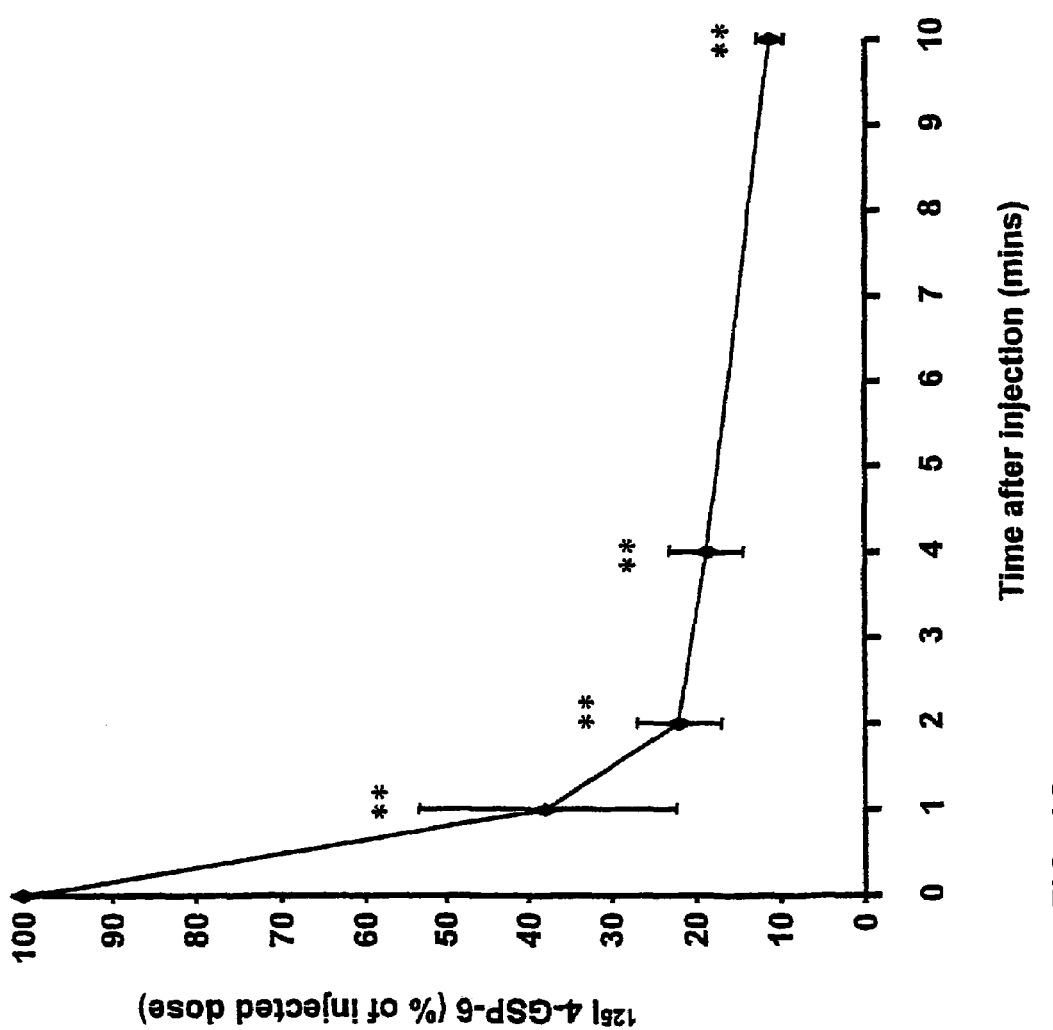
FIG. 13 shows the clearance rate of 4-GSP from the bloodstream within 10 minutes after injection.
Figure 14:
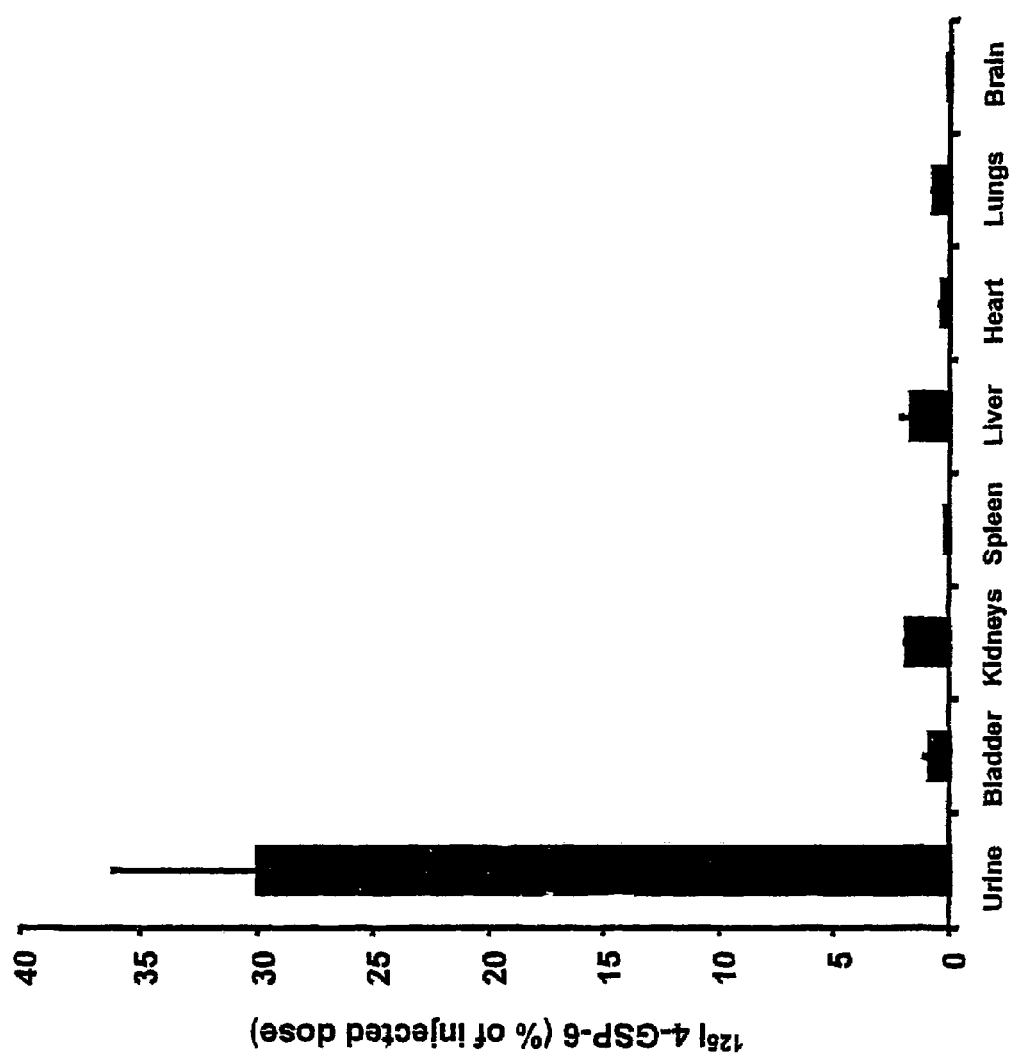
FIG. 14 shows the accumulation of 4-GSP-6 in various organs within 10 minutes after injection.

In order to inhibit rolling, selectin antagonists must remain intact at sufficient concentrations in the blood. $^{125}$I-radiolabelled 4-GSP-6 was used to investigate the kinetics of clearance from the circulation. A mixture of radiolabelled and unlabelled 4-GSP-6 were injected into the jugular vein giving a final 4-GSP-6 dose of 4.3 µmol/kg. Blood samples (10 µl) were drawn from the carotid artery at serial time points after application of material and counted in a gamma counter. More than 60% of injected 4-GSP-6 was cleared from the blood within 1 min of injection (FIG. 13). Following an initial rapid fall in blood concentration, a more gradual clearance is seen between 2 and 10 min. After collection of the final blood sample, mice were rapidly killed and various organs and fluids harvested. Approximately 30% of injected 4-GSP-6 can be detected in the urine within 10 min of its application at 4.3 µmol/kg. Subsequent HPLC analysis demonstrated that 4-GSP-6 was intact in the urine (not shown). Examination of various organs showed little evidence of preferential accumulation at sites other than the urine (FIG. 14).

In summary, glycosulfopeptides of the present invention can reverse pre-existing, surgically induced leukocyte rolling. This observation is consistent with a model wherein soluble selectin binding molecules compete with cell bound ligands preventing the formation of new bonds required for continued maintenance of leukocyte rolling. Since surgically induced rolling is P-selectin-dependent, these data demonstrate that 2-GSP-6 and 4-GSP-6 are active P-selectin antagonists in vivo.

Studies with $^{125}$I-labeled 4-GSP-6 demonstrated that glycosulfopeptides are rapidly cleared from the circulation (FIG. 13). Only 20% of injected material remained in the blood 2 min after intravenous injection whereas our first count of rolling flux was made between one and two min. When these factors are accounted for and blood volume of a mouse is estimated at 8% of body weight, then blood concentration of 4-GSP-6 2 min after injection of 4.3 µmol/kg would be approximately 10 µM. Considering that a significant portion of this material may be bound to blood elements, this figure compares quite closely with the dose of 4-GSP-6 required to inhibit neutrophil binding to P-selectin in vitro (4.7 µM).

Design of the clearance studies (blood sampling for 10 min followed by sacrifice and organ harvest) was optimized for detailed tracking of GSP removal from the blood rather than accumulation elsewhere. Nevertheless, it appears clear that nonconjugated 4-GSP-6 rapidly disappears from the blood and a significant portion of material is cleared to the urine within 10 min. Conjugation of the GSP will reduce rate of clearance of the GSP (see below). No preferential accumulation in other organs harvested was seen but it was assumed that remaining material is distributed fairly evenly throughout the body. The fact that a high dose (12.9 µmol/kg) of 4-GSP-6 caused a sustained increase of leukocyte rolling velocity suggests that material cleared from the blood and into tissues slowly returns to the blood and is cleared to the urine more gradually. Application via routes other than intravenous as well as other methods described herein may be one way to prolong the activity and reduce clearance of glycosulfopeptides.

It has been recently demonstrated that a recombinant PSGL-1 chimera (a recombinant PSGL-1 fragment fused to IgG, known commercially as rPSGL-Ig) can also competitively reverse existing P-selectin dependent leukocyte rolling. Instantaneous activity of GSPs compares favorably with that of rPSGL-Ig in that 4.3 µmol/kg (equating to approximately 15 mg/kg) gives 50–70% inhibition of leukocyte rolling whereas 30 mg/kg rPSGL-Ig is required for a similar effect. Differences in molecular weight notwithstanding, the activity of the GSP is all the more remarkable when clearance kinetics are considered (rPSGL-Ig has a half life of hundreds of hours). Activity of the GSP also compares favorably with less selective inhibitors such as fucoidin.

Utility

The present invention provides a method for the treatment of a patient afflicted with inflammatory diseases or other such diseases or conditions characterized at least in part by leukocyte rolling wherein such disease states or conditions may be treated by the administration of a therapeutically effective amount of a glycosulfopeptide compound of the present invention as described herein to a subject in need thereof. In one embodiment the glycosulfopeptide is SEQ ID NO:53.

The term "inflammation" is meant to include reactions of both the specific and non-specific defense systems. A specific defense system reaction is a specific immune system reaction response to an antigen. Examples of a specific defense system reaction include the antibody response to antigens such as rubella virus, and delayed-type hypersensitivity response mediated by T-cells (as seen, for example, in individuals who test "positive" in the Mantaux test).

A non-specific defense system reaction is an inflammatory response mediated by leukocytes incapable of immunological memory. Such cells include granulocytes, macrophages, neutrophils, for example. Examples of a non-specific defense system reaction include the immediate swelling at the site of a bee sting, the reddening and cellular infiltrate induced at the site of a burn and the collection of PMN leukocytes at sites of bacterial infection (e.g., pulmonary infiltrates in bacterial pneumonias, pus formation in abscesses).

Although the invention is particularly suitable for cases of acute inflammation, it also has utility for chronic inflammation. Types of inflammation that can be treated with the present invention include diffuse inflammation, traumatic inflammation, immunosuppression, toxic inflammation, specific inflammation, reactive inflammation, parenchymatous inflammation, obliterative inflammation, interstitial inflammation, croupous inflammation, and focal inflammation.

It will be appreciated that the glycosulfopeptides described herein will be used in methods of diagnosis, monitoring, and treatment of inflammatory disease processes involving leukocyte rolling including rheumatoid arthritis, acute and chronic inflammation, post-ischemic (reperfusion) leukocyte-mediated tissue damage, atherosclerosis, acute leukocyte-mediated lung injury (e.g., Adult Respiratory Distress Syndrome), and other tissue-or organ-specific forms of acute inflammation (e.g., glomerulonephritis). In other embodiments, the glycosulfopeptides contemplated herein will be used to (1) reduce restenosis in patients undergoing percutaneous coronary interventions such as angioplasty and stenting; (2) reduce the sequelae of deep venous thrombosis such as leg swelling, pain, and ulcers; (3) reduce mortality in patients with myocardial infarction; (4) improve organ transplant survival by inhibiting early ischemia-reperfusion injury; (5) reduce pulmonary complications and cognitive disorders in patients undergoing heart-lung bypass during coronary artery bypass graft surgery; (6) treat patients having sickle cell disease.

A therapeutically effective amount of a compound of the present invention refers to an amount which is effective in controlling, reducing, or promoting the inflammatory response. The term "controlling" is intended to refer to all processes wherein there may be a slowing, interrupting, arresting, or stopping of the progression of the disease and does not necessarily indicate a total elimination of all disease symptoms.

The term "therapeutically effective amount" is further meant to define an amount resulting in the improvement of any parameters or clinical symptoms characteristic of the inflammatory response. The actual dose will be different for the various specific molecules, and will vary with the patient's overall condition, the seriousness of the symptoms, and counter indications.

As used herein, the term "subject" or "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount of a compound of the present invention also refers to an amount of the compound which is effective in controlling or reducing an inflammatory response or another condition described herein dependent at least in part on leukocyte rolling.

A therapeutically effective amount of the compositions of the present invention will generally contain sufficient active ingredient (i.e., the glycosulfopeptide portion of the conjugated or non-conjugated glycosulfopeptide) to deliver from about 0.1 µg/kg to about 100 mg/kg (weight of active ingredient/body weight of patient). Preferably, the composition will deliver at least 0.5 µg/kg to 50 mg/kg, and more preferably at least 1 µg/kg to 10 mg/kg.

Practice of the method of the present invention comprises administering to a subject a therapeutically effective amount of the active ingredient, in any suitable systemic or local formulation, in an amount effective to deliver the dosages listed above. An effective, particularly preferred dosage of the glycosulfopeptide (for example, GSP-6, 2-GSP-6 or 4-GSP-6) for substantially inhibiting activated neutrophils is 1 µg/kg to 1 mg/kg of the active ingredient. The dosage can be administered on a one-time basis, or (for example) from one to five times per day or once or twice per week, or continuously via a venous drip, depending on the desired therapeutic effect.

As noted, preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally or parenterally (i.e., subcutaneously, intravenously, intramuscularly, intraperitoneally, or intratracheally).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

Additional pharmaceutical methods may be employed to control the duration of action. Increased half-life and controlled release preparations may be achieved through the use of polymers to conjugate, complex with, or absorb the glycosulfopeptide described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl)methacrylamide, and the appropriate concentration of macromolecules as well as the methods of incorporation, in order to control release.

Another possible method useful in controlling the duration of action by controlled release preparations and half-life is incorporation of the glycosulfopeptide molecule or its functional derivatives into particles of a polymeric material such as polyesters, polyamides, polyamino acids, hydrogels, poly(lactic acid), ethylene vinylacetate copolymers, copolymer micelles of, for example, PEG and poly(l-aspartamide).

The half-life of the glycosulfopeptides described herein can be extended by their being conjugated to other molecules such as polymers using methods known in the art to form drug-polymer conjugates. For example, the GSPs can be bound to molecules of inert polymers known in the art, such as a molecule of polyethylene glycol (PEG) in a method known as "pegylation". Pegylation can therefore extend the in vivo lifetime and thus therapeutic effectiveness of the glycosulfopeptide molecule. Pegylation also reduces the potential antigenicity of the GSP molecule. Pegylation can also enhance the solubility of GSPs thereby improving their therapeutic effect. PEGs used may be linear or branched-chain.

PEG molecules can be modified by functional groups, for example as shown in Harris et al., "Pegylation, A Novel Process for Modifying Phararmacokinetics", *Clin Pharmacokinet*, 2001:40(7); 539–551, and the amino terminal end of the GSP, or cysteine residue if present, or other linking amino acid therein can be linked thereto, wherein the PEG molecule can carry one or a plurality of one or more types of GSP molecules or, the GSP can carry more than one PEG molecule.

By "pegylated GSP" is meant a glycosulfopeptide of the present invention having a polyethylene glycol (PEG) moiety covalently bound to an amino acid residue or linking group of the peptide backbone of the GSP.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the GSP, and/or can be linked to an amino acid residue downstream of the N-terminal amino acid, such as lysine, histidine, tryptophan, aspartic acid, glutamic acid, and cysteine, for example or other such amino acids known to those of skill in the art. Cysteine-pegylated GSPs, for example, are created by attaching polyethylene glycol to a thio group on a cysteine residue of the GSP.

The chemically modified GSPs contain at least one PEG moiety, preferably at least two PEG moieties, up to a maximum number of PEG moieties bound to the GSP without abolishing activity, e.g., the PEG moiety(ies) are bound to an amino acid residue preferably at or near the N-terminal portion of the GSP.

The PEG moiety attached to the protein may range in molecular weight from about 200 to 20,000 MW. Preferably the PEG moiety will be from about 1,000 to 8,000 MW, more preferably from about 3,250 to 5,000 MW, most preferably about 5,000 MW.

The actual number of PEG molecules covalently bound per chemically modified GSP of the invention may vary widely depending upon the desired GSP stability (i.e. serum half-life).

Glycosulfopeptide molecules contemplated herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference.

Alternatively, it is possible to entrap the glycosulfopeptides in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences*.

U.S. Pat. No. 4,789,734 describe methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a glycosulfopeptide composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of a GSP, i.e., that amount necessary for preventative or curative health measures. If the pharmaceutical preparation is to be employed as a reagent or diagnostic, then it should contain reagent or diagnostic amounts of a GSP.

All of the assay methods listed herein are well within the ability of one of ordinary skill in the art given the teachings provided herein.

All references, patents and patent applications cited herein are hereby incorporated herein in their entirety by reference.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings.

SEQUENCE LISTING

```
<160> NUMBER OF SEQ ID NOS: 56

<210> SEQ ID NO 1
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (8)..(8)
```

<223> OTHER INFORMATION: tyrosine having a sulfate linked thereto
<220> FEATURE:
<221> NAME/KEY: MISC_FEATURE
<222> LOCATION: (11)..(11)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide R group
    linked thereto

<400> SEQUENCE: 1

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 2
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide R group
    linked thereto

<400> SEQUENCE: 2

Gly Gln Ala Thr Glu Xaa Glu Xaa Leu Asp Tyr Asp Phe Leu Pro Glu
1               5                   10                  15

Xaa Glu Pro Pro Glu Met Leu
            20

<210> SEQ ID NO 3
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (11)..(11)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide R group
    linked thereto

<400> SEQUENCE: 3

Gly Gln Ala Thr Glu Xaa Glu Tyr Leu Asp Xaa Asp Phe Leu Pro Glu
1               5                   10                  15

Xaa Glu Pro Pro Glu Met Leu
            20

<210> SEQ ID NO 4

```
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (11)..(11)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide R group
      linked thereto

<400> SEQUENCE: 4

Gly Gln Ala Thr Glu Tyr Glu Xaa Leu Asp Xaa Asp Phe Leu Pro Glu
1               5                  10                  15

Xaa Glu Pro Pro Glu Met Leu
            20

<210> SEQ ID NO 5
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (11)..(11)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide linked
      thereto

<400> SEQUENCE: 5

Gly Gln Ala Thr Glu Tyr Glu Tyr Leu Asp Xaa Asp Phe Leu Pro Glu
1               5                  10                  15

Xaa Glu Pro Pro Glu Met Leu
            20

<210> SEQ ID NO 6
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide R group
      linked thereto

<400> SEQUENCE: 6

Gly Gln Ala Thr Glu Tyr Glu Xaa Leu Asp Tyr Asp Phe Leu Pro Glu
1               5                  10                  15

Xaa Glu Pro Pro Glu Met Leu
            20

<210> SEQ ID NO 7
```

-continued

```
<211> LENGTH: 23
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (17)..(17)
<223> OTHER INFORMATION: threonine having an oligosaccharide R group
      linked thereto

<400> SEQUENCE: 7

Gly Gln Ala Thr Glu Xaa Glu Tyr Leu Asp Tyr Asp Phe Leu Pro Glu
1               5                   10                  15

Xaa Glu Pro Pro Glu Met Leu
            20

<210> SEQ ID NO 8
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 8

Gly Glu Xaa Glu Xaa Leu Asp Xaa Asp Phe Leu Pro Glu Xaa Glu
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 9

Gly Glu Xaa Glu Xaa Leu Asp Tyr Asp Phe Leu Pro Glu Xaa Glu
1               5                   10                  15
```

```
<210> SEQ ID NO 10
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 10

Gly Glu Xaa Glu Tyr Leu Asp Xaa Asp Phe Leu Pro Glu Xaa Glu
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 11

Gly Glu Tyr Glu Xaa Leu Asp Xaa Asp Phe Leu Pro Glu Xaa Glu
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 12

Gly Glu Tyr Glu Tyr Leu Asp Xaa Asp Phe Leu Pro Glu Xaa Glu
1               5                   10                  15

<210> SEQ ID NO 13
<211> LENGTH: 15
<212> TYPE: PRT
<213> ORGANISM: Artificial sequence
```

```
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 13

Gly Glu Tyr Glu Xaa Leu Asp Tyr Asp Phe Leu Pro Glu Xaa Glu
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 14

Gly Glu Xaa Glu Tyr Leu Asp Tyr Asp Phe Leu Pro Glu Xaa Glu
1               5                   10                  15

<210> SEQ ID NO 15
<211> LENGTH: 22
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (10)..(10)
<223> OTHER INFORMATION: tyrosine having a sulfate linked thereto
<220> FEATURE:
<221> NAME/KEY: MISC_FEATURE
<222> LOCATION: (16)..(16)
<223> OTHER INFORMATION: threonine having an oligosaccharide R group
      linked thereto

<400> SEQUENCE: 15

Gln Ala Thr Glu Xaa Glu Xaa Leu Asp Xaa Asp Phe Leu Pro Glu Xaa
1               5                   10                  15

Glu Pro Pro Glu Met Leu
            20

<210> SEQ ID NO 16
<211> LENGTH: 21
<212> TYPE: PRT
<213> ORGANISM: Artificial sequence
<220> FEATURE:
<223> OTHER INFORMATION: Completely synthesized
```

```
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 16

Ala Thr Glu Xaa Glu Xaa Leu Asp Xaa Asp Phe Leu Pro Glu Xaa Glu
1               5                   10                  15

Pro Pro Glu Met Leu
            20

<210> SEQ ID NO 17
<211> LENGTH: 21
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (10)..(10)
<223> OTHER INFORMATION: tyrosine having a sulfate linked thereto
<220> FEATURE:
<221> NAME/KEY: MISC_FEATURE
<222> LOCATION: (16)..(16)
<223> OTHER INFORMATION: threonine having an oligosaccharide R group
      linked thereto

<400> SEQUENCE: 17

Gln Ala Thr Glu Xaa Glu Xaa Leu Asp Xaa Asp Phe Leu Pro Glu Xaa
1               5                   10                  15

Glu Pro Pro Glu Met
            20

<210> SEQ ID NO 18
<211> LENGTH: 20
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
```

```
<221> NAME/KEY: MISC_FEATURE
<222> LOCATION: (14)..(14)
<223> OTHER INFORMATION: threonine having an oligosaccharide R group
      linked thereto

<400> SEQUENCE: 18

Thr Glu Xaa Glu Xaa Leu Asp Xaa Asp Phe Leu Pro Glu Xaa Glu Pro
1               5                   10                  15

Pro Glu Met Leu
            20

<210> SEQ ID NO 19
<211> LENGTH: 20
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (10)..(10)
<223> OTHER INFORMATION: tyrosine having a sulfate linked thereto
<220> FEATURE:
<221> NAME/KEY: MISC_FEATURE
<222> LOCATION: (16)..(16)
<223> OTHER INFORMATION: threonine having an oligosaccharide R group
      linked thereto

<400> SEQUENCE: 19

Gln Ala Thr Glu Xaa Glu Xaa Leu Asp Xaa Asp Phe Leu Pro Glu Xaa
1               5                   10                  15

Glu Pro Pro Glu
            20

<210> SEQ ID NO 20
<211> LENGTH: 19
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 20

Glu Xaa Glu Xaa Leu Asp Xaa Asp Phe Leu Pro Glu Xaa Glu Pro Pro
1               5                   10                  15

Glu Met Leu
```

```
<210> SEQ ID NO 21
<211> LENGTH: 19
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (10)..(10)
<223> OTHER INFORMATION: tyrosine having a sulfate linked thereto
<220> FEATURE:
<221> NAME/KEY: MISC_FEATURE
<222> LOCATION: (16)..(16)
<223> OTHER INFORMATION: threonine having an oligosaccharide R group
      linked thereto

<400> SEQUENCE: 21

Gln Ala Thr Glu Xaa Glu Xaa Leu Asp Xaa Asp Phe Leu Pro Glu Xaa
1               5                   10                  15

Glu Pro Pro

<210> SEQ ID NO 22
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: threonine having an oligosaccharide R group
      linked thereto

<400> SEQUENCE: 22

Xaa Glu Xaa Leu Asp Xaa Asp Phe Leu Pro Glu Xaa Glu Pro Pro Glu
1               5                   10                  15

Met Leu

<210> SEQ ID NO 23
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
```

```
<221> NAME/KEY: MISC_FEATURE
<222> LOCATION: (10)..(10)
<223> OTHER INFORMATION: tyrosine having a sulfate linked thereto
<220> FEATURE:
<221> NAME/KEY: MISC_FEATURE
<222> LOCATION: (16)..(16)
<223> OTHER INFORMATION: threonine having an oligosaccharide R group
      linked thereto

<400> SEQUENCE: 23

Gln Ala Thr Glu Xaa Glu Xaa Leu Asp Xaa Asp Phe Leu Pro Glu Xaa
1               5                   10                  15

Glu Pro

<210> SEQ ID NO 24
<211> LENGTH: 17
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (10)..(10)
<223> OTHER INFORMATION: tyrosine having a sulfate linked thereto
<220> FEATURE:
<221> NAME/KEY: MISC_FEATURE
<222> LOCATION: (16)..(16)
<223> OTHER INFORMATION: threonine having an oligosaccharide R group
      linked thereto

<400> SEQUENCE: 24

Gln Ala Thr Glu Xaa Glu Xaa Leu Asp Xaa Asp Phe Leu Pro Glu Xaa
1               5                   10                  15

Glu

<210> SEQ ID NO 25
<211> LENGTH: 20
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 25

Ala Thr Glu Xaa Glu Xaa Leu Asp Xaa Asp Phe Leu Pro Glu Xaa Glu
1               5                   10                  15

Pro Pro Glu Met
```

```
                           20

<210> SEQ ID NO 26
<211> LENGTH: 19
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 26

Thr Glu Xaa Glu Xaa Leu Asp Xaa Asp Phe Leu Pro Glu Xaa Glu Pro
1               5                   10                  15

Pro Glu Met

<210> SEQ ID NO 27
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 27

Glu Xaa Glu Xaa Leu Asp Xaa Asp Phe Leu Pro Glu Xaa Glu Pro Pro
1               5                   10                  15

Glu Met

<210> SEQ ID NO 28
<211> LENGTH: 17
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
```

```
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: threonine having an oligosaccharide R group
      linked thereto

<400> SEQUENCE: 28

Xaa Glu Xaa Leu Asp Xaa Asp Phe Leu Pro Glu Xaa Glu Pro Pro Glu
1               5                   10                  15

Met

<210> SEQ ID NO 29
<211> LENGTH: 19
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 29

Ala Thr Glu Xaa Glu Xaa Leu Asp Xaa Asp Phe Leu Pro Glu Xaa Glu
1               5                   10                  15

Pro Pro Glu

<210> SEQ ID NO 30
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 30

Thr Glu Xaa Glu Xaa Leu Asp Xaa Asp Phe Leu Pro Glu Xaa Glu Pro
```

Pro Glu

<210> SEQ ID NO 31
<211> LENGTH: 17
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 31

Glu Xaa Glu Xaa Leu Asp Xaa Asp Phe Leu Pro Glu Xaa Glu Pro Pro
1               5                   10                  15

Glu

<210> SEQ ID NO 32
<211> LENGTH: 16
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: threonine having an oligosaccharide R group
      linked thereto

<400> SEQUENCE: 32

Xaa Glu Xaa Leu Asp Xaa Asp Phe Leu Pro Glu Xaa Glu Pro Pro Glu
1               5                   10                  15

<210> SEQ ID NO 33
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE

```
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 33

Ala Thr Glu Xaa Glu Xaa Leu Asp Xaa Asp Phe Leu Pro Glu Xaa Glu
1               5                   10                  15

Pro Pro

<210> SEQ ID NO 34
<211> LENGTH: 17
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 34

Thr Glu Xaa Glu Xaa Leu Asp Xaa Asp Phe Leu Pro Glu Xaa Glu Pro
1               5                   10                  15

Pro

<210> SEQ ID NO 35
<211> LENGTH: 16
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 35

Glu Xaa Glu Xaa Leu Asp Xaa Asp Phe Leu Pro Glu Xaa Glu Pro Pro
```

<210> SEQ ID NO 36
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: threonine having an oligosaccharide R group
      linked thereto

<400> SEQUENCE: 36

Xaa Glu Xaa Leu Asp Xaa Asp Phe Leu Pro Glu Xaa Glu Pro Pro
1               5                   10                  15

<210> SEQ ID NO 37
<211> LENGTH: 17
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 37

Ala Thr Glu Xaa Glu Xaa Leu Asp Xaa Asp Phe Leu Pro Glu Xaa Glu
1               5                   10                  15

Pro

<210> SEQ ID NO 38
<211> LENGTH: 16
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto

```
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 38

Thr Glu Xaa Glu Xaa Leu Asp Xaa Asp Phe Leu Pro Glu Xaa Glu Pro
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 39

Glu Xaa Glu Xaa Leu Asp Xaa Asp Phe Leu Pro Glu Xaa Glu Pro
1               5                   10                  15

<210> SEQ ID NO 40
<211> LENGTH: 14
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: tyrosine having a sulfate linked thereto

<400> SEQUENCE: 40

Xaa Glu Xaa Leu Asp Xaa Asp Phe Leu Pro Glu Xaa Glu Pro
1               5                   10

<210> SEQ ID NO 41
<211> LENGTH: 16
<212> TYPE: PRT
<213> ORGANISM: Artificial sequence
```

```
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 41

Ala Thr Glu Xaa Glu Xaa Leu Asp Xaa Asp Phe Leu Pro Glu Xaa Glu
 1               5                  10                  15

<210> SEQ ID NO 42
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 42

Thr Glu Xaa Glu Xaa Leu Asp Xaa Asp Phe Leu Pro Glu Xaa Glu
 1               5                  10                  15

<210> SEQ ID NO 43
<211> LENGTH: 14
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto
```

<400> SEQUENCE: 43

Glu Xaa Glu Xaa Leu Asp Xaa Asp Phe Leu Pro Glu Xaa Glu
1               5                   10

<210> SEQ ID NO 44
<211> LENGTH: 13
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: threonine having an oligosaccharide R group
      linked thereto

<400> SEQUENCE: 44

Xaa Glu Xaa Leu Asp Xaa Asp Phe Leu Pro Glu Xaa Glu
1               5                   10

<210> SEQ ID NO 45
<211> LENGTH: 15
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (9)..(9)
<223> OTHER INFORMATION: tyrosine having a sulfate linked thereto
<220> FEATURE:
<221> NAME/KEY: MISC_FEATURE
<222> LOCATION: (15)..(15)
<223> OTHER INFORMATION: threonine having an oligosaccharide R group
      linked thereto

<400> SEQUENCE: 45

Ala Thr Glu Xaa Glu Xaa Leu Asp Xaa Asp Phe Leu Pro Glu Xaa
1               5                   10                  15

<210> SEQ ID NO 46
<211> LENGTH: 14
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE

```
<222> LOCATION: (5)..(5)
<223> OTHER INFORMATION: tyrosine having a sulfate linked thereto
<220> FEATURE:
<221> NAME/KEY: MISC_FEATURE
<222> LOCATION: (8)..(8)
<223> OTHER INFORMATION: tyrosine having a sulfate linked thereto
<220> FEATURE:
<221> NAME/KEY: MISC_FEATURE
<222> LOCATION: (14)..(14)
<223> OTHER INFORMATION: threonine having an oligosaccharide R group
      linked thereto

<400> SEQUENCE: 46

Thr Glu Xaa Glu Xaa Leu Asp Xaa Asp Phe Leu Pro Glu Xaa
1               5                   10

<210> SEQ ID NO 47
<211> LENGTH: 13
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 47

Glu Xaa Glu Xaa Leu Asp Xaa Asp Phe Leu Pro Glu Xaa
1               5                   10

<210> SEQ ID NO 48
<211> LENGTH: 12
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: tyrosine having a sulfate linked thereto
<220> FEATURE:
<221> NAME/KEY: MISC_FEATURE
<222> LOCATION: (3)..(3)
<223> OTHER INFORMATION: tyrosine having a sulfate linked thereto
<220> FEATURE:
<221> NAME/KEY: MISC_FEATURE
<222> LOCATION: (6)..(6)
<223> OTHER INFORMATION: tyrosine having a sulfate linked thereto
<220> FEATURE:
<221> NAME/KEY: MISC_FEATURE
<222> LOCATION: (12)..(12)
<223> OTHER INFORMATION: threonine having an oligosaccharide R group
      linked thereto

<400> SEQUENCE: 48

Xaa Glu Xaa Leu Asp Xaa Asp Phe Leu Pro Glu Xaa
1               5                   10

<210> SEQ ID NO 49
```

```
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 49

Glu Xaa Glu Xaa Leu Asp Xaa Asp Phe Leu Pro Glu Xaa Glu Pro Pro
1               5                   10                  15

Glu Cys

<210> SEQ ID NO 50
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 50

Glu Xaa Glu Xaa Leu Asp Xaa Asp Phe Leu Pro Glu Xaa Glu Pro Pro
1               5                   10                  15

Glu Cys

<210> SEQ ID NO 51
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
```

```
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having a GalNAc
      linked thereto

<400> SEQUENCE: 51

Glu Xaa Glu Xaa Leu Asp Xaa Asp Phe Leu Pro Glu Xaa Glu Pro Pro
1               5                   10                  15

Glu Met

<210> SEQ ID NO 52
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: threonine having an oligosaccharide R group
      linked thereto

<400> SEQUENCE: 52

Glu Xaa Glu Xaa Leu Asp Xaa Asp Phe Leu Pro Glu Xaa Glu Pro Pro
1               5                   10                  15

Glu Met

<210> SEQ ID NO 53
<211> LENGTH: 18
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (2)..(2)
<223> OTHER INFORMATION: tyrosine having a sulfate linked thereto
<220> FEATURE:
<221> NAME/KEY: MISC_FEATURE
<222> LOCATION: (4)..(4)
<223> OTHER INFORMATION: tyrosine having a sulfate linked thereto
<220> FEATURE:
<221> NAME/KEY: MISC_FEATURE
<222> LOCATION: (7)..(7)
<223> OTHER INFORMATION: tyrosine having a sulfate linked thereto
<220> FEATURE:
<221> NAME/KEY: MISC_FEATURE
<222> LOCATION: (13)..(13)
<223> OTHER INFORMATION: an O-, N-, or S-linking amino acid having an
      oligosaccharide R group linked thereto, the R group being a
      sialylated, fucosylated N-acetyl lactosamino glycan

<400> SEQUENCE: 53

Glu Xaa Glu Xaa Leu Asp Xaa Asp Phe Leu Pro Glu Xaa Glu Pro Pro
1               5                   10                  15

Glu Met
```

```
<210> SEQ ID NO 54
<211> LENGTH: 14
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (1)..(1)
<223> OTHER INFORMATION: X is an amino acid selected from the group
      comprising ala, cys, asp, glu, phe, gly, his, ile, lys, leu, met,
      asn, pro, gln, arg, ser, thr, val, trp, or tyr, or is absent
<220> FEATURE:
<221> NAME/KEY: MISC_FEATURE
<222> LOCATION: (13)..(13)
<223> OTHER INFORMATION: X is thr, ser, tyr, met, asn, gln, cys, lys,
      hydroxyproline, or hydroxylysine, or any N-linking, S-linking or
      O-linking amino acid
<220> FEATURE:
<221> NAME/KEY: MISC_FEATURE
<222> LOCATION: (14)..(14)
<223> OTHER INFORMATION: X is an acid selected from the group comprising
      ala, cys, asp, glu, phe, gly, his, ile, lys, leu, met, asn, pro,
      gln, arg, ser, thr, val, trp, or tyr, or is absent

<400> SEQUENCE: 54

Xaa Tyr Glu Tyr Leu Asp Tyr Asp Phe Leu Pro Glu Xaa Xaa
1               5                   10

<210> SEQ ID NO 55
<211> LENGTH: 12
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (12)..(12)
<223> OTHER INFORMATION: X is thr, ser, tyr, met, asn, gln, cys, lys,
      hydroxyproline, or hydroxylysine, or any N-linking, S-linking or
      O-linking amino acid

<400> SEQUENCE: 55

Tyr Glu Tyr Leu Asp Tyr Asp Phe Leu Pro Glu Xaa
1               5                   10

<210> SEQ ID NO 56
<211> LENGTH: 13
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (12)..(12)
<223> OTHER INFORMATION: X is thr, ser, tyr, met, cys, asn, gln, lys,
      hydroxyproline, or hydroxylysine or any N-linking, S-linking or
      O-linking amino acid
<220> FEATURE:
<221> NAME/KEY: MISC_FEATURE
<222> LOCATION: (13)..(13)
<223> OTHER INFORMATION: X is an amino acid selected from the group
      comprising ala, cys, asp, glu, phe, gly, his, ile, lys, leu, met,
      asn, pro, gln, arg, ser, thr, val, trp, or tyr, or is absent

<400> SEQUENCE: 56

Tyr Glu Tyr Leu Asp Tyr Asp Phe Leu Pro Glu Xaa Xaa
1               5                   10
```

What is claimed is:

1. A method of inhibiting or reducing leukocyte rolling in a subject in vivo, comprising:

administering to the subject an effective amount of a compound comprising a glycosulfopeptide thereby inhibiting or reducing leukocyte rolling in the subject, the glycosulfopeptide having 12 to 30 amino acids and comprising the structure (SEQ ID NO:55):

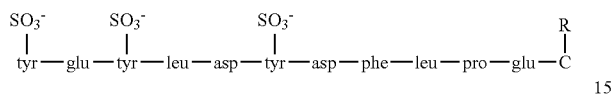

wherein C is an O-, N-, or S-linking amino acid; and wherein R is one of $R_1$, $R_3$–$R_{13}$ or $R_{15}$, wherein:

$R_1$ = 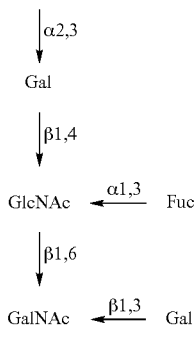

$R_3$ = 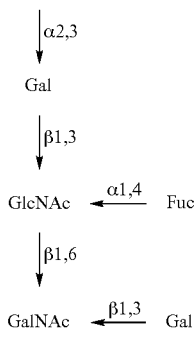

$R_4$ = 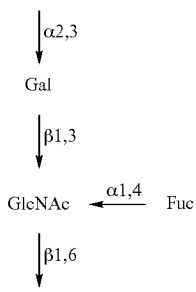

$R_5$ = 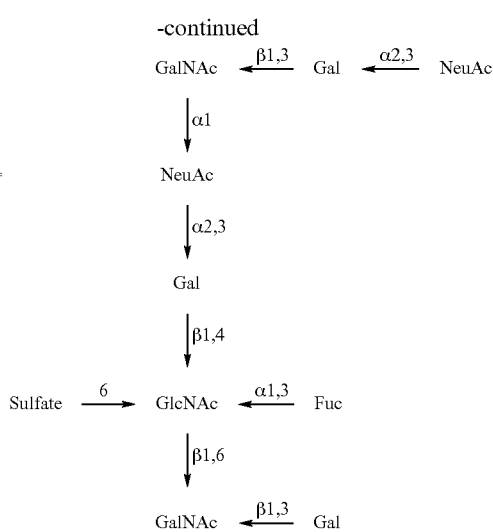

$R_6$ = 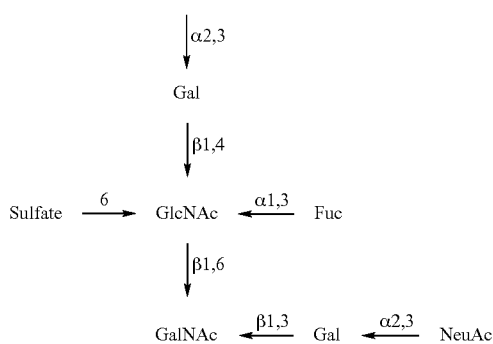

$R_7$ = 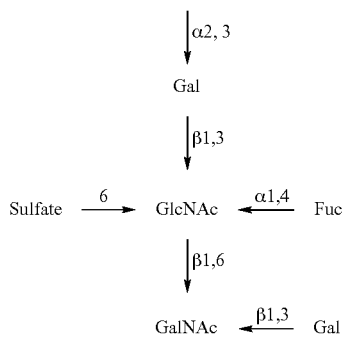

$R_8$ = 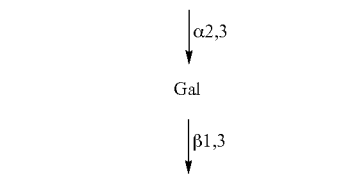

-continued

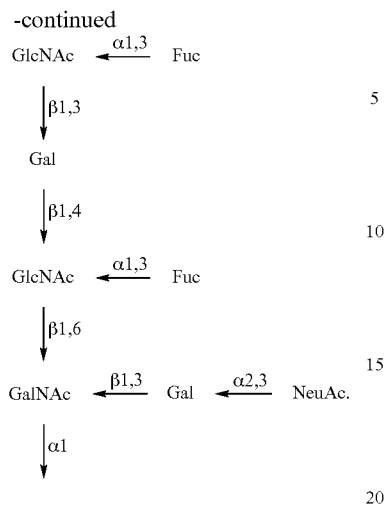

2. The method of claim 1 wherein C is serine, threonine, hydroxyproline, tyrosine, hydroxylysine, methionine, cysteine, lysine, asparagine, or glutamine.

3. The method of claim 1, wherein the glycosulfopeptide is combined with a polymer to form the compound, wherein the polymer is covalently linked to the N-terminal amino acid of the glycosulfopeptide, or to a lysine, histidine, tryptophan, aspartic acid, glutamic acid, or cysteine of the glycosulfopeptide, and wherein the polymer has the function of increasing the half-life of the compound or controlled release of the compound.

4. A composition for inhibiting or reducing leukocyte rolling in a subject in vivo, comprising:
   a pharmaceutically acceptable carrier; and
   a compound comprising a glycosulfopeptide having 12 to 30 amino acids and comprising the structure (SEQ ID NO:55):

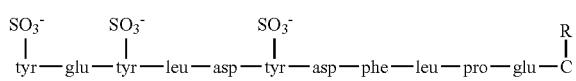

wherein, C is an O-, N-, or S-linking amino acid; and
wherein, R is one of $R_1$, $R_3$-$R_{13}$ or $R_{15}$ wherein:

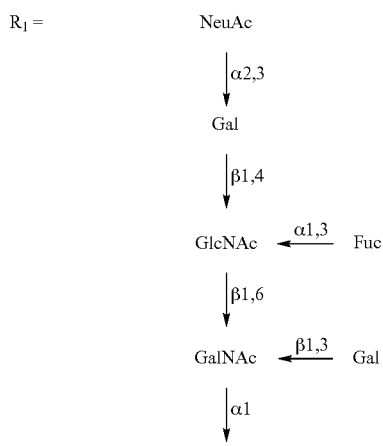

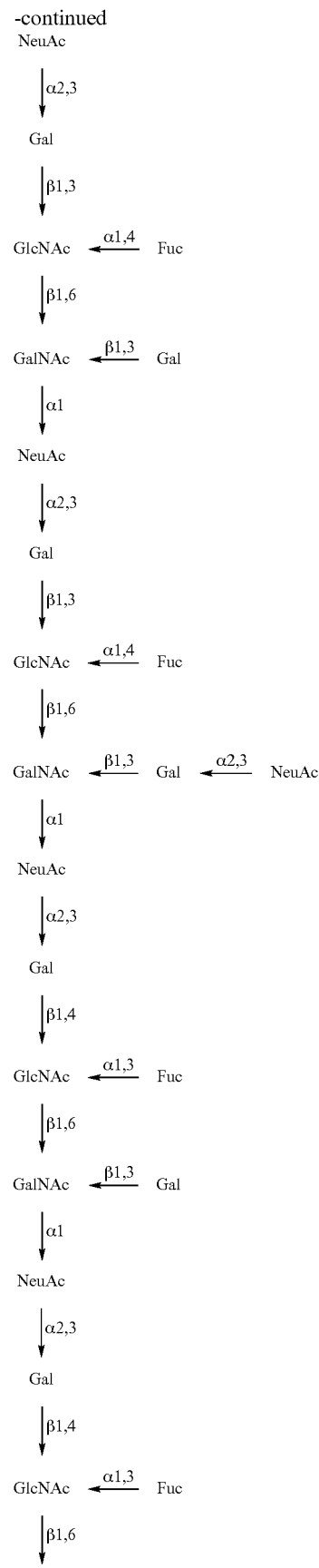

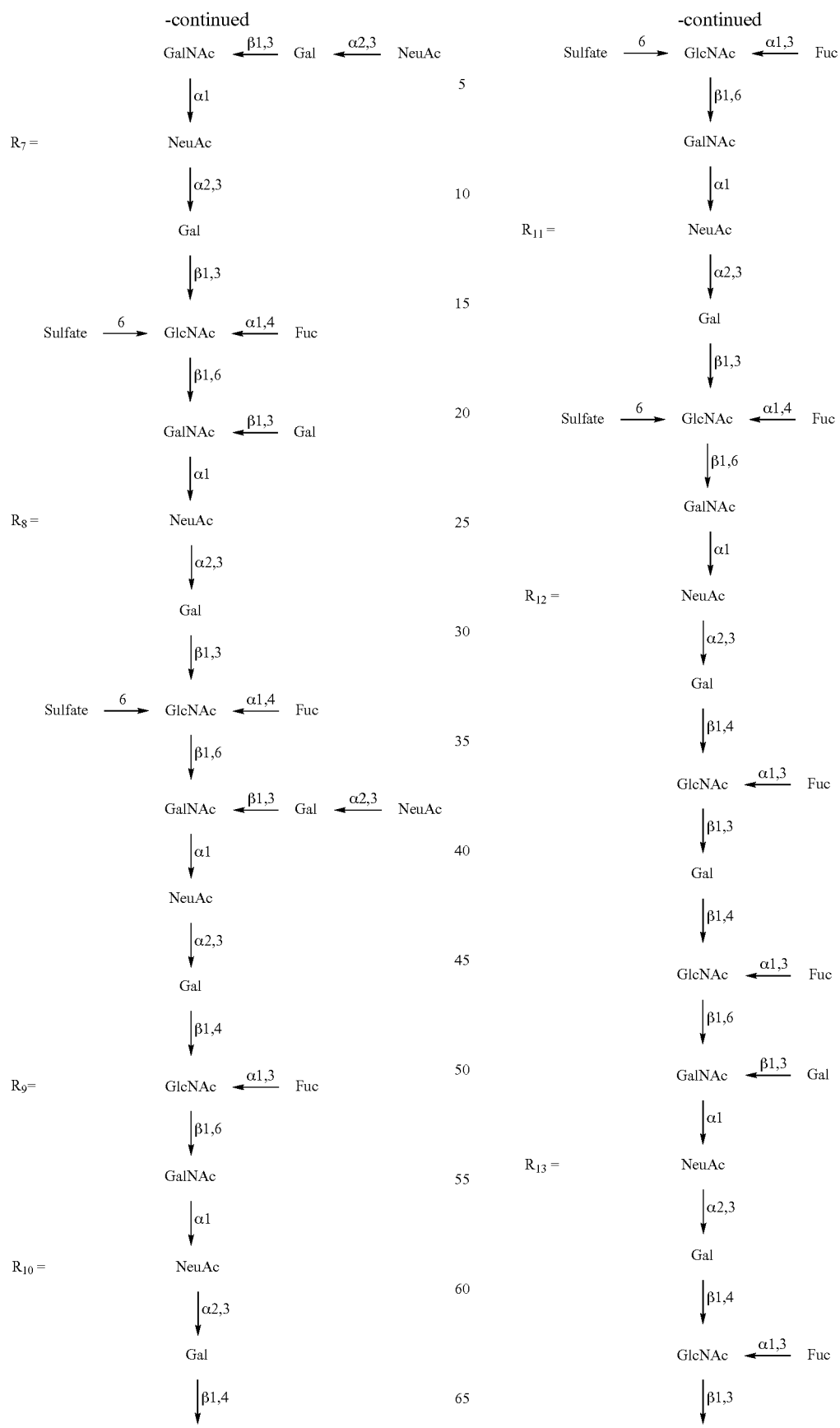

-continued $R_{15} =$ 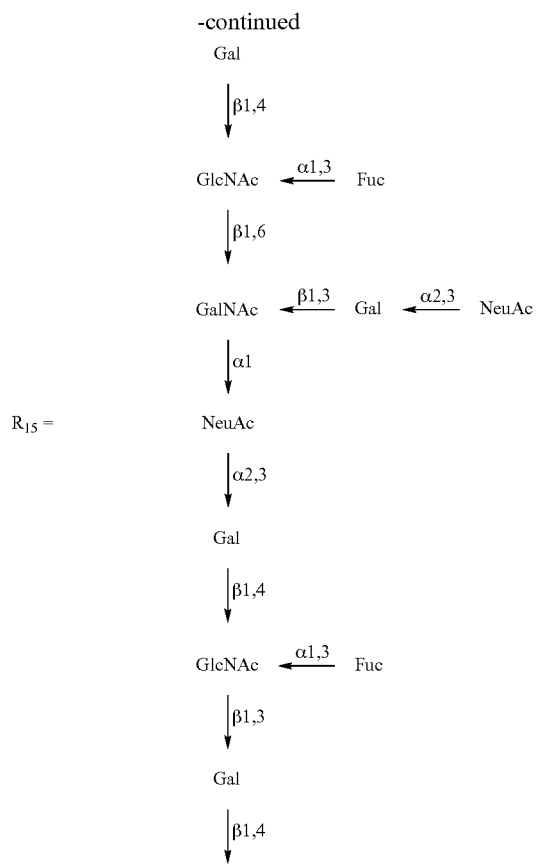

-continued

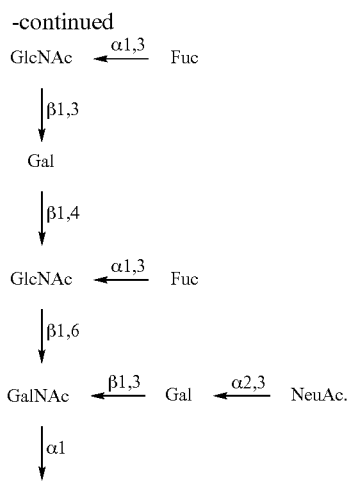

5. The composition of claim 4 wherein C is serine, threonine, hydroxyproline, tyrosine, hydroxylysine, methionine, cysteine, lysine, asparagine, or glutamine.

6. The composition of claim 4, wherein the glycosulfopeptide is combined with a polymer to form the compound, wherein the polymer is covalently linked to the N-terminal amino acid of the glycosulfopeptide, or to a lysine, histidine, tryptophan, aspartic acid, glutamic acid, or cysteine of the glycosulfopeptide, and wherein the polymer has the function of increasing the half-life of the compound or controlled release of the compound.

* * * * *

UNITED STATES PATENT AND TRADEMARK OFFICE
CERTIFICATE OF CORRECTION

PATENT NO. : 7,189,828 B2  Page 1 of 2
APPLICATION NO. : 11/239576
DATED : March 13, 2007
INVENTOR(S) : Richard D. Cummings and Rodger P. McEver It is certified that error appears in the above-identified patent and that said Letters Patent is hereby corrected as shown below:

In the Specification:
Column 2, line 17: Delete "selecting" and replace with -- selectins --
Column 10, line 17: Delete "gin" and replace with -- gln --

In the Sequence Listing:
Column 63, Sequence listing for 55 & 56: Delete entirety of the Sequence listing for SEQ ID NO 55 and SEQ ID NO 56 and replace with

```
--<210>  55
  <211>  12
  <212>  PRT
  <213>  Artificial sequence

<220>
  <223>  Completely synthesized

<220>
  <221>  MISC_FEATURE
  <222>  (1)..(1)
  <223>  tyrosine having a sulfate linked thereto <220>
  <221>  MISC_FEATURE
  <222>  (3)..(3)
  <223>  tyrosine having a sulfate linked thereto <220>
  <221>  MISC_FEATURE
  <222>  (6)..(6)
  <223>  tyrosine having a sulfate linked thereto <220>
  <221>  MISC_FEATURE
  <222>  (12)..(12)
  <223>  thr, ser, tyr, met, asn, gln, cys, lys, hydroxyproline, or
         hydroxylysine, or any N-linking , S-linking or O-linking amino
         acid having an oligosaccharide R group linked thereto

<400>  55

Xaa Glu Xaa Leu Asp Xaa Asp Phe Leu Pro Glu Xaa
1               5                   10

<210>  56
  <211>  13
  <212>  PRT
  <213>  Artificial sequence

<220>
  <223>  Completely synthesized
```

UNITED STATES PATENT AND TRADEMARK OFFICE
CERTIFICATE OF CORRECTION

PATENT NO. : 7,189,828 B2  
APPLICATION NO. : 11/239576  
DATED : March 13, 2007  
INVENTOR(S) : Richard D. Cummings and Rodger P. McEver It is certified that error appears in the above-identified patent and that said Letters Patent is hereby corrected as shown below:

Column 63, Sequence listing for 55 & 56 (cont'd):
```
<220>
<221>  MISC_FEATURE
<222>  (1)..(1)
<223>  tyrosine having a sulfate linked thereto <220>
<221>  MISC_FEATURE
<222>  (3)..(3)
<223>  tyrosine having a sulfate linked thereto <220>
<221>  MISC_FEATURE
<222>  (6)..(6)
<223>  tyrosine having a sulfate linked thereto <220>
<221>  MISC_FEATURE
<222>  (12)..(12)
<223>  thr, ser, tyr, met, cys, asn, gln, lys, hydroxyproline, or
       hydroxylysine or any N-linking, S-linking or O-linking amino acid
       having an oligosaccharide R group linked thereto <220>
<221>  MISC_FEATURE
<222>  (13)..(13)
<223>  an amino acid selected from the group comprising ala, cys, asp,
       glu, phe, gly, his, ile, lys, leu, met, asn, pro, gln, arg, ser,
       thr, val, trp, or tyr, having an oligosaccharide R group linked
       thereto or is absent

<400>  56

Xaa Glu Xaa Leu Asp Xaa Asp Phe Leu Pro Glu Xaa Xaa
1               5                   10
```

Signed and Sealed this

Tenth Day of July, 2007

JON W. DUDAS  
*Director of the United States Patent and Trademark Office*